(12) United States Patent
Sawada et al.

(10) Patent No.: US 6,780,913 B2
(45) Date of Patent: Aug. 24, 2004

(54) ZINC BORATE, AND PRODUCTION METHOD AND USE THEREOF

(75) Inventors: Hiroshi Sawada, Tokyo (JP); Hiroshi Igarashi, Tokyo (JP); Akira Tatebe, Tokyo (JP); Kazunori Sakao, Tokyo (JP)

(73) Assignee: Mizusawa Industrial Chemicals, Ltd., Tokyo (JP)

( * ) Notice: Subject to any disclaimer, the term of this patent is extended or adjusted under 35 U.S.C. 154(b) by 512 days.

(21) Appl. No.: 09/914,789

(22) PCT Filed: Jan. 11, 2001

(86) PCT No.: PCT/JP01/00097

§ 371 (c)(1),
(2), (4) Date: Sep. 5, 2001

(87) PCT Pub. No.: WO01/51418

PCT Pub. Date: Jul. 19, 2001

(65) Prior Publication Data

US 2003/0030042 A1 Feb. 13, 2003

(30) Foreign Application Priority Data

Jan. 11, 2000 (JP) .................................... 2000-002999

(51) Int. Cl.$^7$ ............................ C08K 3/38; C01B 35/10
(52) U.S. Cl. ........................ 524/405; 423/277; 423/278; 423/279; 252/609
(58) Field of Search ...................... 524/405; 423/277, 423/278, 279; 252/609

(56) References Cited

U.S. PATENT DOCUMENTS 6,248,814 B1 * 6/2001 Hironaka et al. ............. 524/80

* cited by examiner

*Primary Examiner*—Edward J. Cain
(74) *Attorney, Agent, or Firm*—Sherman & Shalloway

(57) ABSTRACT

A zinc borate having a particular crystallite size and containing very little sodium components and a method of preparing the same. The zinc borate has a particular chemical composition, has a crystallite size of not smaller than 40 nm as found from diffraction peaks of indexes of planes of (020), (101) and (200) in the X-ray diffraction image (Cu-kα) and contains sodium components in amounts of not larger than 100 ppm as measured by the atomic absorptiometric method.

21 Claims, 25 Drawing Sheets

111
ZINC BORATE, AND PRODUCTION METHOD AND USE THEREOF

TECHNICAL FIELD

The present invention relates to a novel zinc borate, a method of preparing the same and use thereof. More specifically, the invention relates to a novel zinc borate having a particular crystallite size and containing very little sodium components and to a method of preparing the same.

BACKGROUND ART

In recent years, resin molded articles have been used in a wide variety of fields, and it has been desired to impart flame-retarding property to these resins. It has further been desired that the resin molded articles such as building materials produce smoke in suppressed amounts so will not to hinder people from taking refuge in case fire has broken.

It has long been known that a zinc borate exhibits excellent flame-retarding property. For example, Japanese Examined Patent Publication (Kokoku) No. 67363/1981 teaches blending a zinc borate with a metal oxide such as $Al_2O_3$, $SiO_2$, $Sb_2O_3$, ZnO or $ZrO_2$.

Japanese Unexamined Patent Publication (Kokai) No. 137988/1988 filed by the present applicant discloses a flame-retarding composition obtained by treating the surfaces of a zinc borate particles with an oxide, a hydroxide or a basic carbonate of an alkaline earth metal of an amount of 1 to 40% by weight per the whole weight.

A method of preparing a zinc borate has also been long known. For example, Comparative Example 1 of Japanese Examined Patent Publication (Kokoku) No. 20902/1971 teaches the preparation of a compound of the formula, $$2ZnO.3B_2O_3.9H_2O$$

by mixing a combination of borax pentahydrate and boric acid with a zinc oxide in an aqueous solution of sulfuric acid, followed by the addition of seed crystals of a zinc borate.

However, the conventional zinc borate assumes the form of particles of indefinite shapes having relatively large diameters in which fine primary particles are coagulated in a random fashion and densely, and poorly disperses in the resin, fails to impart luster on the surfaces of the molded articles of a resin blended therewith, and offers poor appearance and decreased commercial value.

Further, the known zinc borate has been synthesized in an aqueous medium containing sodium salts and, hence, contains sodium components as impurities in considerably large amounts. When the plastic molded articles for electric and electronic parts are blended with such a zinc borate for a purpose of imparting flame-retarding property, it is probable that the electric properties are deteriorated as represented by poor insulation and dielectric breakdown after the use for extended periods of time being affected by humidity.

DISCLOSURE OF THE INVENTION

It is, therefore, an object of the present invention to provide a zinc borate having a particular crystallite size and containing very little sodium components, and a method of preparing the same.

Another object of the present invention is to provide a zinc borate which excellently disperses in a resin, markedly improves smoothness, luster and appearance of the surfaces of a resin blended therewith, and maintains, on an excellent level, the electric properties of the resin blended therewith as a flame-retarding agent or a smoke-suppressing agent, and a method of preparing the same.

According to the present invention, there is provided a zinc borate having a chemical composition represented by the following formula (1), $$2ZnO.mB_2O_3.XH2O \qquad (1)$$

wherein m is a number of from 2.8 to 3.2, and x is a number of not larger than 4,
and having a crystallite size of not smaller than 40 nm as found from diffraction peaks of indexes of planes of (020), (101) and (200) in the X-ray diffraction (Cu-kα) and containing sodium components in amounts of not larger than 100 ppm as measured by the atomic absorptiometric method.

In the zinc borate according to the present invention, it is desired that the individual particles are independent rhombic hexahedrons, the length of a side of each particle lying in a range of from 0.3 to 7.0 μm as measured by a scanning-type electron microphotograph.

In the zinc borate according to the present invention, it is desired that a product of crystallite sizes as found from the diffraction peaks of indexes of planes (020), (101) and (200) is not smaller than 200,000 $nm^3$, and that a volume-based median diameter as found by a laser diffraction method is in a range of from 1.0 to 6.0 μm.

The invention further provides a method of preparing a zinc borate by forming fine crystals of a zinc borate by reacting a zinc flower and a boric acid at a substantially stoichiometric ratio at a relatively low temperature, effecting the aging as required and, then, maintaining the reaction system at a relatively high temperature to grow the crystals.

According to the present invention, further, there are provided a flame-retarding agent or a flame-retarding assistant, a smoke-suppressing agent, an antibacterial agent and a water glass-curing agent comprising the above zinc borate.

BEST MODE FOR CARRYING OUT THE INVENTION

[Action]

The zinc borate according to the present invention has a chemical composition represented by the following formula (1), $$2ZnO \cdot mB_2O_3 \cdot XH_2O \qquad (1)$$

wherein m is a number of from 2.8 to 3.2, and x is a number of not larger than 4.

A variety kinds of zinc borates have been known, such as, $ZnO \cdot B_2O_3 \cdot 1{\sim}2H_2O$, $2ZnO \cdot 3B_2O_3 \cdot 3{\sim}9H_2O$, $3ZnO \cdot 5B_2O_3 \cdot 14H_2O$, $ZnO \cdot 5B_2O_3 \cdot 4.5H_2O$, $6ZnO \cdot 5B_2O_3 \cdot 3H_2O$.

Among them, however, the present invention deals with the zinc borates of the 2.3 type having the most excellent flame-retarding property (hereinafter those of the 2.3 type are simply referred to as the zinc borates).

The zinc borates according to the present invention exhibit the same X-ray diffraction image as that of the conventional zinc borate of the 2.3 type.

Figure 1:
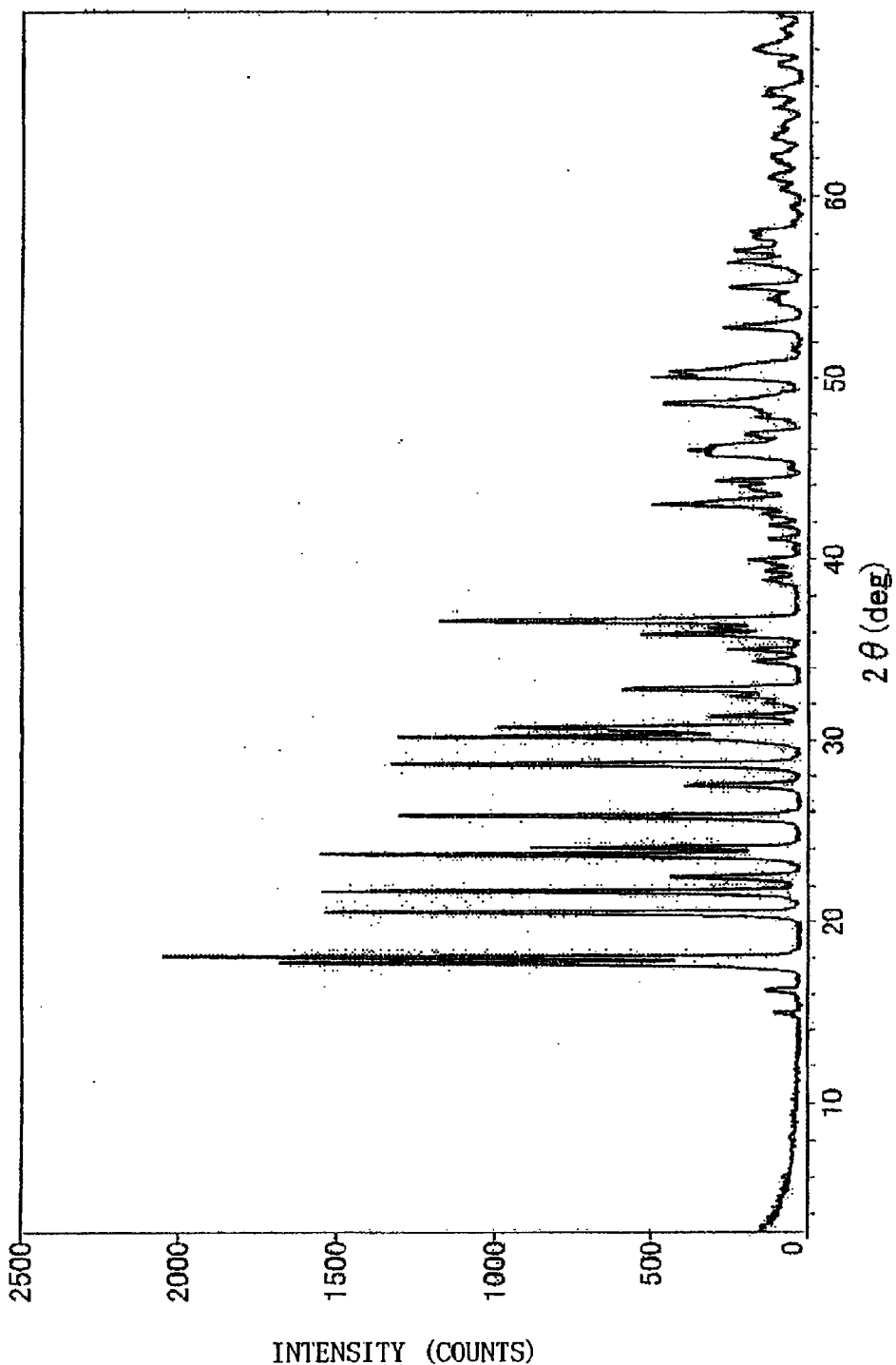
FIG. 1 shows an X-ray diffraction image (Cu-kα) of a zinc borate according to an embodiment 1 of the present invention.

FIG. 1 of an accompanying drawing shows an X-ray diffraction image (Cu-kα) of the zinc borate according to the present invention, and the following Table 1 shows relationships among the spacings, indexes of planes and relative intensities of the diffraction image.

TABLE 1

| 2 θ | Spacing A | Index of a plane | Relative Intensity (I/I$_{100}$) |
|---|---|---|---|
| 18.0 | 4.91 | (020) | 100 |
| 20.6 | 4.31 | (101) | 78.2 |
| 21.7 | 4.08 | (120) | 75.1 |
| 22.5 | 3.95 | (111) | 21.7 |
| 23.7 | 3.75 | (121) | 74.7 |
| 24.1 | 3.69 | (200) | 40.0 |
| 27.5 | 3.32 | (121) | 22.0 |
| 28.7 | 3.11 | (012) | 63.3 |

In the X-ray diffraction of crystals, it has been known that an intensity peak appears in the interference when the following Bragg's formula (2), $$n\lambda = 2d_{hk1} \sin \theta \qquad (2)$$

wherein n is a degree, λ is a wavelength of an X-ray, dhk1 is a spacing of (hk1) of a crystal, and θ is an angle of diffraction, is satisfied, and there also exists a relationship represented by the following Scherrer's formula (3) between the sharpness of the interference peak and the size of the crystal, $$Lhk1 = K\lambda/(H \cos \theta) \qquad (3)$$

wherein Lhk1 is a size of a crystal in a direction perpendicular to a plane (hk1), K is a constant and is about 0.9, H is a half-value width (radian) of an interference peak, and λ and θ are the same as those of the above-mentioned formula (2).

The zinc borate according to the present invention has a feature in that the crystallite sizes found from the diffraction peaks of the indexes of planes (020), (101) and (200) in the X-ray diffraction (Cu-kα) are all not smaller than 40 nm, and that the crystallite sizes are expanded as compared with those of the conventional zinc borates.

The zinc borate of the present invention is compared below in Table 2 with a commercially available zinc borate manufactured by company A concerning their indexes of planes, half-value widths and crystallite sizes.

TABLE 2

| Bragg angle (2 θ) | Index of plane | This Invention | | Product of A Co. | |
|---|---|---|---|---|---|
| | | Half-value width | Crystallite size | Half-value width | Crystallite size |
| 18.03 | 020 | 0.119 | 67.6 | 0.146 | 55.1 |
| 20.54 | 101 | 0.126 | 64.1 | 0.161 | 50.1 |
| 24.10 | 200 | 0.126 | 64.5 | 0.159 | 51.1 |

The zinc borate according to the present invention has an additional feature in that a product of the crystallite sizes as found from the diffraction peaks of indexes of planes (020), (101) and (200) is not smaller than 200,000 nm$^3$ and, particularly, not smaller than 250,000 nm$^3$.

Concerning the zinc borates shown in Table 2, the product of crystallite sizes is found to be 141,062 nm$^3$ in the case of the zinc borate manufactured by the company A, and is 279,489 nm$^3$ in the case of the zinc borate of the present invention, from which it is obvious that the volume of the crystallite is nearly doubled.

It is believed that the size of the crystallite is giving a very favorable effect on the structure of zinc borate particles of definite shapes.

The zinc borate of the invention has a feature in that the individual particles are independent rhombic hexahedrons having a length of a side of each particle in a range of from 0.3 to 7.0 μm as measured by a scanning-type electron microphotograph.

Figure 2:
FIG. 2 is a scanning-type electron microphotograph (magnification: 5000 times) showing the particle structure of the zinc borate according to the embodiment 1 of the present invention.
Figure 5:
FIG. 5 is a scanning-type electron microphotograph (magnification: 5000 times) showing the particle structure of the zinc borate according to the embodiment 2 of the present invention.
Figure 6:
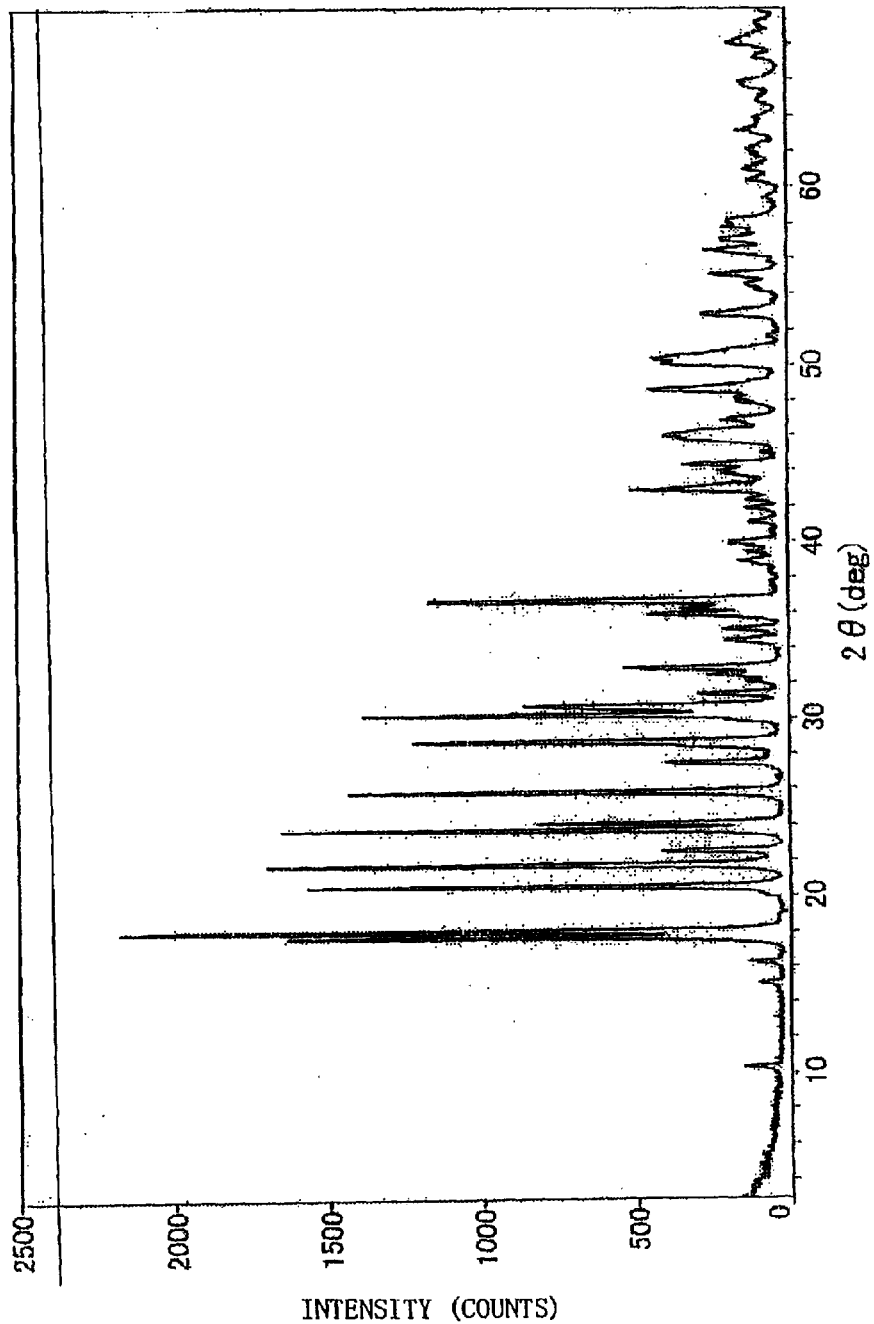
FIG. 6 shows an X-ray diffraction image (Cu-kα) of a zinc borate according to an embodiment 3 of the present invention.

In the accompanying drawings, FIG. 2 is a scanning-type electron microphotograph illustrating the structure of particles of zinc borate of the present invention, FIG. 5 is a scanning-type electron microphotograph illustrating the structure of particles of a commercially available zinc borate manufactured by the company A, and FIG. 6 is a scanning-type electron microphotograph illustrating the structure of particles of a commercially available zinc borate manufactured by the company B.

These photographs tell the facts that the known zinc borate particles have relatively large diameters and indefinite shapes with fine primary particles coagulated in a random fashion and densely, while the zinc borate particles according to the present invention are independent rhombic hexahedrons having definite shapes.

It will be further understood that the zinc borate according to the invention has a length of a side of each rhombic hexahedron of from 0.3 to 7.0 μm and, particularly, from 0.3 to 2.0 μm, the particle diameter thus being suppressed to be small offering excellent uniformity in the particle diameter.

It is obvious that the zinc borate according to the present invention belongs to a so-called polycrystalline one since the crystallite size is greatly different from the real particle size. It should, however, be noted that the crystalline zinc borate of the present invention features a very high regularity in the arrangement of zinc borate crystallites.

Figure 3:
FIG. 3 is a scanning-type electron microphotograph (magnification: 7000 times) showing, on an enlarged scale, the particle structure of the zinc borate according to the present invention.

FIG. 3 which is an attached drawing is a scanning-type electron microphotograph (magnification: 7000 times) illustrating, on an enlarged scale, the structure of crystals of the zinc borate according to the present invention.

As will obvious from the above X-ray diffraction image, the zinc borate crystals belong to the monoclinic system. The zinc borate particles shown in FIG. 3 obviously has the structure of a rhombic hexahedron which is that of the monoclinic system, which is quite the same as a single crystal that cannot be distinguished, in appearance, from an aggregate of crystals.

Owing to the above crystal structure and particle structure, the zinc borate of the present invention offers the following advantages. That is, the conventional zinc borate poorly disperses in the resin, fails to impart luster on the surfaces of the molded articles of a resin blended therewith, and offers poor appearance and decreased commercial value. Owing to the above crystal structure and particle structure, however, the zinc borate of the present invention excellently disperses in the resin, imparts smoothness and luster onto the surfaces of the molded articles of the resin blended therewith and, further, strikingly improves the appearance.

Being associated with the above crystal structure and particle structure, the zinc borate of the present invention further gives excellent advantages such as imparting flame-retarding property and smoke-suppressing property inherent in the zinc borate.

Being also associated with the method of its preparation, the zinc borate of the present invention has such a feature that the content of sodium component is not larger than 100 ppm, preferably, not larger than 50 ppm and, more preferably, not larger than 30 ppm as measured by the atomic absorptiometric method.

For instance, the above-mentioned zinc borate manufactured by the company A has a sodium content of 350 ppm, whereas the zinc borate of a particle structure shown in FIG. 3 has a sodium content of 15 ppm, which is a reduction to 1/20 or less of sodium content.

Deterioration in the electric properties of a resin composition blended with a zinc borate can be evaluated by a promotion testing being immersed in hot water. In the promotion testing in Example appearing later, for example, a resin composition blended with 10 parts of the zinc borate manufactured by the company A exhibits a volume resistivity (80° C.) of $4.06 \times 10^{13}$ whereas the resin composition blended with 10 parts by weight of the zinc borate of the invention exhibits a volume resistivity (80° C.) of $8.02 \times 10^{13}$, thus obviously imparting flame-retarding property and smoke-suppressing property while maintaining electric properties of the resin composition blended with the zinc borate on an excellent level.

In preparing the zinc borate according to the present invention, a zinc flower and a boric acid are reacted together at a substantially stoichiometric ratio and at a relatively low temperature such as from 45 to 65° C. to form fine crystals of zinc borate, followed, as required, by aging to grow the crystals while maintaining the reaction system at a relatively high temperature, such as 70 to 100° C.

The method of the present invention selects a zinc flower and a boric acid as starting materials for synthesis in order to avoid the infiltration of electric property-deteriorating components such as sodium as much as possible. In order to synthesize the zinc borate having the above-mentioned crystal structure and particle structure from the above starting materials, it is also important that these two starting materials are reacted together at a substantially stoichiometric ratio.

In the present invention, it is important that the reaction is conducted in two steps. First, the two are reacted together at a low temperature to prepare fine crystalline zinc borate. In conducting the synthesis, formation of fine crystalline zinc borate can be easily confirmed by an increase in the viscosity of the reaction system.

Then, the formed fine crystals are aged by maintaining, as required, the reaction system at the reaction temperature in the first step or at a temperature slightly higher than the above temperature and, then, the crystals are grown by maintaining the reaction system at a temperature higher than the reaction temperature in the first step. Further, the reaction in the first step may be conducted by adding seed crystals of zinc borate in an amount of from 0.5 to 10 parts by weight per 100 parts by weight of the $B_2O_3$ component of boric acid, in order to shorten the reaction time.

Concretely speaking, when there exists no seed crystal, it is desired to conduct the reaction in the first step at a temperature of from 40 to 75° C. and, preferably, from 45 to 70° C. and to conduct the reaction in the second step at a temperature of from 70 to 120° C. and, preferably, from 75 to 110° C. When there exist seed crystals, it is desired to conduct the reaction in the first step at a temperature of from 45 to 70° C. and, preferably, from 50 to 70° C. and to conduct the reaction in the second step at a temperature of from 75 to 120° C. and, preferably, from 75 to 110° C.

According to the present invention which conducts the reaction in two steps as described above, it is allowed to prepare the zinc borate having the above-mentioned crystal structure and particle structure.

The zinc borate according to the present invention can be effectively used as a flame-retarding agent or a flame-retarding assistant, a smoke-suppressing agent, an antibacterial agent, a water glass-curing agent and the like agents.

Among these uses, the zinc borate of the invention is effectively used being blended in the resin to express properties of the above-mentioned agents.

As the resin to be blended with, there can be exemplified any thermoplastic resin, elastomer, thermosetting resin or blends thereof. The zinc borate according to the present invention is used in an amount of from 1 to 150 parts by weight and, particularly, from 3 to 30 parts by weight per 100 parts by weight of the resin. The zinc borate exhibits excellent flame-retarding effect since ① the dehydrating endothermic reaction due to thermal decomposition lowers the temperature of combustion, and ② zinc works as a catalyst for the dehalogenation reaction, promotes the formation of a carbonized layer and suppresses the generation of smoke.

As the thermoplastic resin, there can be used a resin synthesized by using a metallocene catalyst, as well as polyolefins such as low-density polyethylene, high-density polyethylene, polypropylene, poly-1-butene, poly-4-methyl-1-pentene and α-olefin random or block copolymers like ethylene, propylene, 1-butene and 4-methyl-1-pentene; styrene resins such as ethylene/vinyl acetate copolymer, ethylene/vinyl alcohol copolymer, polystyrene, acrylonitrile/styrene copolymer, ABS, and α-methyl styrene/styrene copolymer; polyvinyl compounds such as methyl acrylate and methyl polymethacrylate; polyamides such as nylon 6, nylon 6-6, nylon 6-10, nylon 11 and nylon 12; thermoplastic polyesters such as polyethylene terephthalate and polybutylene terephthalate; polycarbonate; polyphenylene oxide; or mixtures thereof. In particular, the zinc borate of the present invention exhibits a great effect when it is used being blended in a chlorine-containing polymer. As the chlorine-containing polymer, there can be exemplified polymers such as polyvinyl chloride, polyvinylidene chloride, chlorinated polyethylene, chlorinated polypropylene, chlorinated rubber, vinyl chloride/vinyl acetate copolymer, vinyl chloride/ethylene copolymer, vinyl chloride/propylene copolymer, vinyl chloride/styrene copolymer, vinyl chloride/isobutylene copolymer, vinyl chloride/vinylidene chloride copolymer, vinyl chloride/styrene/acrylonitrile copolymer, vinyl chloride/butadiene copolymer, vinyl chloride/propylene chloride copolymer, vinyl chloride/vinylidene chloride/vinyl acetate tercopolymer, vinyl chloride/styrene/maleic anhydride tercopolymer, vinyl chloride/acrylic acid ester copolymer, vinyl chloride/maleic acid ester copolymer, vinyl chloride/methacrylic acid ester copolymer, vinylchloride/acrylonitrile copolymer and internally plasticized polyvinyl chloride; as well as blends of these chlorine-contained polymers with polyethylene, polybutene, ethylene/vinyl acetate copolymer, ethylene/propylene copolymer, polystyrene, acrylic resin, acrylonitrile/butadiene/styrene copolymer, or acrylic acid ester/butadiene/styrene copolymer.

As the elastomer, there can be exemplified nitrile/butadiene rubber (NBR), styrene/butadiene rubber (SBR), chloroprene rubber (CR), polybutadiene (BR), polyisoprene (IIB), butyl rubber, natural rubber, ethylene/propylene rubber (EPR), ethylene/propylene/diene rubber (EPDM), polyurethane, silicone rubber and acrylic rubber; and thermoplastic elastomers such as styrene/butadiene/styrene block copolymer, styrene/isoprene/styrene block copolymer, hydrogenated styrene/butadiene/styrene block copolymer, and hydrogenated styrene/isoprene/styrene block copolymer.

As the thermosetting resin, there can be exemplified phenol-formaldehyde resin, furan-formaldehyde resin, xylene-formaldehyde resin, ketone-formaldehyde resin, urea-formaldehyde resin, melamine-formaldehyde resin, alkyd resin, unsaturated polyester resin, epoxy resin, bismaleimide resin, triallylcyanurate resin, thermosetting acrylic resin, silicone resin and urethane resin. These resins can be used alone or in a combination of two or more kinds. In particular, the epoxy resin generally refers to monomers, oligomers and polymers having two or more epoxy groups in one molecule thereof, but is not to limit their molecular weights or molecular structures. Its examples include biphenyl epoxy compound, bisphenol epoxy compound, phenol novolak epoxy resin, cresol novolak resin, triphenolmethane epoxy compound and alkyl-modified triphenolmethane epoxy compound, which may be used alone or being mixed together.

The zinc borate of the invention has a feature in that the component of sodium component is not larger than 100 ppm, preferably, not larger than 50 ppm and, more preferably, not larger than 30 ppm as measured by the atomic absorptiometric method, and is best suited for an epoxy resin for sealing semiconductor. When an epoxy resin is used, the curing agent is, preferably, phenol novolak resin, dicyclopentadiene-modified phenol resin, paraxylylene-modified phenol resin or terpene-modified phenol resin, and the curing-promoting agent is, preferably, 1,8-diazabicycloundecene, triphenylphosphine, benzyldimethylamine or 2-methylimidazole.

The zinc borate of the present invention can be used being blended in a resin, the zinc borate being used in a single kind as a flame-retarding component or being used in combination with one or more of other flame-retarding agents such as aluminum hydroxide, magnesium hydroxide, hydrotalcite compound, zinc-modified hydrotalcite-like compound, lithium aluminum composite hydroxide salt, polybasic aluminum magnesium salt, zinc-modified polybasic aluminum magnesium salt, dawsonite, polyhydric alcohol, polyhydric alcohol partial ester and epoxy compound. Those having hardnesses smaller than that of the zinc borate may be ground with the flame-retarding agent, and may be applied to the surfaces of the zinc borate of the invention. In this case, the amount of application is from 0.5 to 50 parts by weight and, preferably, from 0.5 to 30 parts by weight per 100 parts by weight of the zinc borate.

For example, the mixing under the grinding condition by using an alkaline earth metal compound stands for a mixing in which an alkaline earth metal compound is ground with zinc borate particles, and the zinc borate particles are smeared with fine particles of the alkaline earth metal compound formed by the grinding. In the grind-mixing, the zinc borate particles are very harder than the alkaline earth metal compound and, hence, work as a pulverizing medium for the alkaline earth metal compound.

Henschel's mixer, super mixer, tube mill, ball mill, vibration mill, pin mill, mixing and grinding machine or atomizer can be used for the grind-mixing.

[Hydrotalcite]

Hydrotalcite is a synthetic mineral that belongs to an aluminum magnesium carbonate hydroxide, and there is used a composite metal hydroxide having the following general formula (4), $$M2_xM3_y(OH)_{2x+3y-2z}(A^{2-})_z \cdot AH_2O \tag{4}$$

wherein M2 is a divalent metal ion such as Mg, M3 is a trivalent metal ion such as Al, $A^{2-}$ is a divalent anion such as $CO_3$, and x, y, z are positive numbers satisfying $8 \geq x/y \geq 1/4$ and $z/x+y > 1/20$, and a is a number satisfying $0.25 \leq a/x+y \leq 1.0$.

Among these composite metal hydroxides, a compound represented by the following formula (5), $$Mg_6Al_2(OH)_{16}(CO_3) \cdot 4H_2O \tag{5}$$

is a natural mineral known as hydrotalcite. This mineral and homologues are synthesized by methods taught in Japanese Examined Patent Publication (Kokoku) Nos. 32198/1972, 29477/1973 and 29478/1973 filed by Kyowa Kagaku Co.

In particular, it has been known that a compound represented by the following formula (6), $$Mg_{4.5}Al_2(OH)_{13}(CO_3) \cdot 3H_2O \tag{6}$$

exhibits excellent chlorine ion-trapping property.

It is also allowable to use a compound in which perhalogen oxyacid ions are introduced by utilizing a property that the hydrotalcites are easily ion-exchanged in a state in which they have been dispersed well in water, i.e., by utilizing a property that the carbonic acid ions are exchanged with other anions.

Concretely, the hydrotalcite compounds have composition formulas $Mg_5Al_2(OH)_{16}CO_3 \cdot 4H_2O$, $Mg_{4.5}Al_2(OH)_{13}CO_3 \cdot 3.5H_2O$, $Mg_{0.66}Al_{0.34}(OH)_2(SiO_3)_{0.17} \cdot 0.52H_2O$, $Mg_{0.7}Al_{0.3}(OH)_2(CO_3)_{0.15} \cdot 0.55H_2O$, etc. They have such trade names as Alkamizer 1, Alkamizer 2, Alkamizer 3, Alkamizer 4, DHT-4A, Kyoword, etc.

As the polyhydric alcohol that constitutes a polyhydric alcohol and polyhydric alcohol partial ester, there can be exemplified ethylene glycol, diethylene glycol, triethylene glycol, polyethylene glycol, trimethylene glycol, tetramethylene glycol, hexamethylene glycol, neopentyl glycol, glycerin, diglycerin, dipentaerythritol, manitol, sorbitol, trimethylolpropane, ditrimethylolpropane, trisisocyanurate, monopentaerythritol, and dipentaerythritol adipate. Preferably, there is used a monopentaerythritol having an average particle diameter of from 0.1 to 100 μm.

Further, the above polyhydric alcohols and esters thereof may be used alone or in a combination of at least one or more kinds selected out of them.

In addition to the above, there can be used oxides, hydroxides or sulfates of antimony, zirconium and molybdenum, zinc stannate, zinc hydroxystannate, halogen-containing flame-retarding agent, phosphoric acid ester-type flame-retarding agent and halogenophosphoric acid ester-type flame-retarding agent in one kind or in a combination of two or more kinds.

As the antimony-type flame-retarding agent, there can be favorably used antimony trioxide, antimony pentoxide and sodium antimonate. There can be further used trimethyl stilbene, triethyl stilbene and triphenyl stilbene.

As the zinc stannate-type or zinc hydroxystannate-type flame-retarding agent, there is used a composition represented by the formula (7), $$ZnSnO_3 \text{ or } ZnSn(OH)_6 \tag{7}$$

As the halogen-type flame-retarding agent, there can be exemplified aliphatic halide compounds such as 1,2-dichloroethane, 1,2-dibromoethane, 1,1,2,2-tetrachloroethane, 1,1,2,2-tetrabromoethane, hexachloroethane, hexabromoethane, dibromotetrachloroethane, 1,2,3,4-tetrachlorobutane, 1,2,3,4-tetrabromobutane, chlorinated paraffin and brominated paraffin; aliphatic halogen compounds such as pentabromomonochlorocyclohexane, hexabromocyclohexane, hexachlorocyclohexane, hexabromocyclodecane, hexachlorocyclodecane, hexachlorocyclopentadiene, hexabromocyclopentadiene, chloroendoic acid, diallyl chloroendoate, anhydrous chloroendoic acid and similar iodine compounds; and aromatic halogen compounds such as hexabromobenzene, hexachlorobenzene, pentabromomethylbenzene, pentachloromethylbenzene, hexabromodiphenyl, hexachlorodiphenyl, hexabromodiphenyl ether, hexachlorodiphenyl ether, dibromocredylglycidyl ether, decabromobiphenyl ether, decachlorobiphenyl ether, decabromodiphenyl oxide, decachlorodiphenyl oxide, octabromodiphenyl ether, octachlorodiphenyl ether, tribromophenol, trichlorophenol, tetrabromobisphenol A, tetrachlorobisphenol A, tetrabromobisphenol F, tetrabromobisphenol AD, dibromodichlorobisphenol A, diacetate of tetrabromobisphenol A, diacetate of tetrachlorobisphenol A, tetrabromo-2,2-bis(4,4'-dimethoxyphenyl)propane, tetrachloro-2,2-bis(4,4'-dimethoxyphenyl)propane, tetrabromophthalic anhydride, tetrachlorophthalic anhydride, chlorinated epoxy novolak phenol resin, brominated epoxy novolak phenol resin, brominated bisphenol A epoxy resin and similar iodine compounds.

As the phosphoric acid ester-type flame-retarding agent, there can be exemplified trimethyl phosphate, triethyl phosphate, tributyl phosphate, trioctyl phosphate, tributoxyethyl phosphate, octyldiphenyl phosphate, tricresyl phosphate, triphenyl phosphate and cresyldiphenyl phosphate.

As the halogenophosphoric acid ester-type flame-retarding agent, there can be exemplified tris(chloroethyl) phosphate, tris(2-chloropropyl)phosphate, tris(2,3-dichloropropyl)phosphate, tris(2,3-dibromopropyl) phosphate, and tris(bromochloropropyl)phosphate.

From the standpoint of suppressing the generation of smoke and imparting flame-retarding property, it is desired to use these frame-retarding agents at a weight ratio of from 1:20 to 20:1 and, particularly, from 1:10 to 10:1 relative to the zinc borate. Even in case fire has broken, the flame-retarding property and smoke-suppressing property facilitate evacuation, rescue operation and fire-extinguishing activity.

When a chlorine-contained polymer is used as a resin, it is desired that the resin is blended with a smoke-suppressing agent together with known blending agents such as plasticizer, lubricant, main heat stabilizer, assistant stabilizer, coloring agent, aging stabilizer, aging-retarding agent, photo-stabilizer, ultraviolet ray-absorbing agent, antistatic agent, reinforcing agent, reforming resin or rubber, basic inorganic metal salt, chelate agent, antioxidant, epoxy compound and other reinforcing agents or fillers.

As the plasticizer, there can be used the ones that have been known as a plasticizer for chlorine-contained polymers, such as phthalic acid ester, trimellitic acid ester, pyromellitic acid ester, aliphatic dibasic acid ester, phosphoric acid ester, hydroxypolyhydric carboxylic acid ester, monoaliphatic acid ester, polyhydric alcohol ester, epoxy-type plasticizer and polyester-type plasticizer.

As the lubricant, there can be used a variety of waxes such as petroleum wax, polyethylene wax, polypropylene wax, fatty acid or derivatives thereof, and plant waxes.

The amounts of blending the plasticizer and the lubricant vary depending upon the use of the chlorine-contained polymer, i.e., depending upon the soft blending or the hard blending. In the former case, the plasticizer is blended in an amount of from 20 to 100 parts by weight and, particularly, from 30 to 80 parts by weight and the lubricant is blended in an amount of from 0.05 to 5 parts by weight and, particularly, from 0.5 to 3 parts by weight per 100 parts by weight of the resin. In the latter case, the plasticizer is blended in an amount of from 0 to 10 parts by weight and, particularly, from 0 to 5 parts by weight and the lubricant is blended in an amount of from 0.1 to 5 parts by weight and, particularly, from 0.2 to 3 parts by weight per 100 parts by weight of the resin.

As the main stabilizer, there can be used known ones, such as lead-type stabilizers and non-lead-type stabilizers in a single kind or in two or more kinds in combination.

As the lead-type stabilizer, there can be used any known ones and, particularly, tribasic to tetrabasic lead sulfate, basic lead phosphite, basic lead silicate, basic lead carbonate, basic lead maleate, basic lead phthalate, basic lead stearate, and higher fatty acid lead, which may be used in two or more kinds in combination.

As the non-lead-type stabilizer, there can be exemplified inorganic non-lead-type stabilizer, metal soap-type stabilizer and organotin-type stabilizer. As the inorganic non-lead-type stabilizer, there can be used alkaline earth metal silicate-type stabilizer, alkaline earth metal aluminosilicate-type stabilizer, and alkaline earth metal or zinc-aluminum composite hydroxide carbonate.

Preferred examples of the alkaline earth metal silicate-type stabilizer include a fine crystalline calcium silicate having a chemical composition represented by the general formula (8),

$$CaO.xSiO_2.NH_2O \quad (8)$$

wherein x is a number of not smaller than 0.5, and n is a number of not larger than 2.5,
and having X-ray diffraction images in a spacing of from 3.01 to 3.08 angstroms, in a spacing of from 2.78 to 2.82 angstroms and in a spacing of from 1.81 to 1.84 angstroms, or a composite product thereof with a polyhydric alcohol. Preferred examples of the polyhydric alcohol include pentaerythritol and dipentaerythritol.

Suitable examples of the alkaline earth metal aluminosilicate-type stabilizer include those of the A-type, X-type, Y-type, L-type, P-type, T-type (nepheline), as well as those of various crystal structures, such as offretite, erionite, mordenite, ferrierite, clinoptirolite, chabazite, analcime and aluminosilicate of the sodalite group. However, A-type zeolite is particularly preferred from the standpoint of hydrogen chloride-trapping property.

As the metal soap-type stabilizer, there are used calcium stearate, magnesium stearate, barium stearate and zinc stearate in a single kind or in a combination of two or more kinds.

As the organotin-type stabilizer, there are used dibutyltin dilaurate, dibutyltin maleate, organotin mercaptide, di-n-octyltin laurate, di-n-octyltin maleate polymer, di-n-octyltinbis-2-ethylhexyl maleate, and di-n-octyltinbisisooctylthio glycolate.

It is desired that the above stabilizers are used in an amount of from 0.1 to 20 parts by weight and, particularly, from 0.5 to 10 parts by weight per 100 parts by weight of the resin from the standpoint of heat stability and preventing the initial coloring.

The stabilizers may be used in a single kind or in a combination of two or more kinds. From the standpoint of not decreasing the oxygen index concentration of the chlorine-contained polymer, however, it is desired to use chiefly an inorganic stabilizer.

It is desired that the chlorine-contained polymer composition is further blended with β-diketone or β-keto acid ester in an amount of from 0.05 to 10 parts by weight and, particularly, from 0.1 to 3 parts by weight per 100 parts by weight of the resin. Use the above chelating agent component effectively prevents the initial coloring.

As the β-diketone or β-ketoacid ester, there can be used, for example, 1,3-cyclohexadion, methylenebis-1,3-cyclohexadion, 2-benzyl-1,3-cyclohexadion, acetyltetralon, palmitoyltetralon, stearoyltetralon, benzoyltetralon, 2-acetylcyclohexanone, 2-benzoylcyclohexanone, 2-acetyl-1,3-cyclohexanedion, bis(benzoyl)methane, benzoyl-p-chlorobenzoylmethane, bis(4-methylbenzoyl)methane, bis(2-hydroxybenzoyl)methane, benzoylacetone, tribenzoylmethane, diacetylbenzoylmethane, stearoylbenzoylmethane, palmtoylbenzoylmethane, lauroylbenzoylmethane, dibenzoylmethane, bis(4-chlorobenzoyl)methane, bis(methylene-3,4-dioxybenzoyl)methane, benzoylacetylphenylmethane, stearoyl(4-methoxybenzoyl)methane, butanoylacetone, distearoylmethane, acetylacetone, stearoylacetone, bis(cyclohexanoyl)methane and dipivaloylmethane.

It is further desired that the chlorine-contained polymer composition and the polyolefin-type resin contain, in addition to the above components, a phenol-type antioxidant in an amount of from 0.005 to 3 parts by weight and, particularly, from 0.01 to 0.5 parts by weight per 100 parts by weight of the resin component. The antioxidant is effective in improving the heat stability and in suppressing the heat degradation caused by the chain reaction.

As the phenol-type antioxidant, there can be used either a bisphenol-type antioxidant or a steric hindrance phenol-type antioxidant. Examples include bisphenol A, bisphenol B, bisphenol F, 2,6-diphenyl-4-octadecyloxyphenol, stearyl(3,5-di-tertiary butyl-4-hydroxyphenyl)propionate, distearyl(3,5-di-tertiary butyl-4-hydroxybenzyl)phosphonate, 1,6-hexamethylenebis[(3,5-di-tertiary butyl-4-hydroxyphenyl)propionate], 1,6-hexamethylenebis[(3,5-di-tertiary butyl-4-hydroxyphenyl)amide propionate], bis[3,3-bis(4-hydroxy-3-tertiary butylphenyl)butylic acid]glycol ester, 1,1,3-tris(2-methyl-4-hydroxy-5-tertiary butylphenyl)butane, 1,3,5-tris(2,6-dimethyl-3-hydroxy-4-tertiary butylbenzyl)isocyanurate, 1,3,5-tris(3,5-di-tertiary butyl-4-hydroxybenzyl)isocyanurate, and triethylene glycolbis[(3-tertiary butyl-4-hydroxy-5-methylphenyl)propionate].

As the ultraviolet ray-absorbing agent, there can be exemplified 2-hydroxybenzophenones such as 2,4-dihydroxybenzophenone, 2-hydroxy-4-methoxybenzophenone, and 5,5'-methylenebis(2-hydroxy-4-methoxybenzophenone); and 2-(2'-hydroxyphenyl)benzotriazoles such as 2-(2'-hydroxy-5'-methylphenyl)benzotriazole, 2-(2'-hydroxy-3'-tertiary butyl-5'- methylphenyl)-5-chlorobenzotriazole, 2-(2'-hydroxy-5'-tertiary octylphenyl)benzotriazole, 2-(2'-hydroxy-3',5'-dicumylphenyl)benzotriazole, and 2,2'-methylenebis(4-tertiary octyl-6-benzotriazolyl)phenol.

As the photo stabilizer, there can be exemplified hindered amine photo stabilizers, such as 1,2,2,6,6-pentamethyl-4-piperidyl stearate, 2,2,6,6-tetramethyl-4-piperidyl benzoate, N-(2,2,6,6-tetramethyl-4-piperidyl)dodecylimide succinate, 1-[(3,5-di-tertiary butyl-4-hydroxyphenyl) propionyloxyethyl]-2,2,6,6-tetramethyl-4-piperidyl-(3,5-di-tertiary butyl-4-hydroxyphenyl)propionate, bis(2,2,6,6-tetramethyl-4-piperidyl)sebacate, tetra(2,2,6,6-tetramethyl-4-piperidyl)butanetetracarboxylate, tetra(1,2,2,6,6-pentamethyl-4-piperidyl)butanetetracarboxylate, bis(2,2,6,6-tetramethyl-4-piperidyl)-di(tridecyl)butane tetracarboxylate and bis(1,2,2,6,6-penamethyl-4-piperidyl)-di(tridecyl)butane tetracarboxylate.

To blend a chlorine-contained polymer or the like polymer with the above components to be blended, the components to be blended except plasticizer and/or lubricant are blended in advance as a one-package blending agent which, as required is granulated, and is mixed into the chlorine-contained polymer together with the plasticizer and/or the lubricant by using a kneader such as roll mixer, Bumbery's mixer or pelletizer to obtain a hard composition for molding pipes or a soft composition for covering the electric wires, or to obtain a plastisol, which is then molded into films, sheets, tiles or any other molded articles by calender machining, melt-extrusion molding or slash-molding, or is used for coating.

Further, the zinc borate of the present invention can be used as an antibacterial agent or a water glass-curing agent. In the field of use as antibacterial agents, the zinc borate of the invention can be used as fiber products such as film or sheet for holding freshness (atmosphere sterilization, controlling bacteria), polyester, polyethylene, polypropylene, nylon and acrylic resin; building materials such as antibacterial paper, corrugated cardboard (eradicating bacteria, controlling bacteria, controlling fungi), wall materials, ceiling materials, carpeting materials, floor materials, mats and roof underlying materials; toiletries, cosmetics, paints (eradicating bacteria, controlling bacteria, controlling fungi), splash or spray type bacteria eradicator, goods for kitchen and bath room (bags, containers, cooking board, drainboard, etc.), fishing nets and algae-controlling agent. The zinc borate can be further used being mixed in a cement mortar or a cement concrete to produce antibacterial cement mortar and cement concrete (inclusive of products produced on the site). The zinc borate can be further used for a variety of products for controlling bacteria.

The zinc borate of the present invention having a particular crystallite size and containing very small amounts of sodium component, disperses excellently in a resin, markedly improves smoothness and luster on the surfaces of the resin blended therewith, and works to greatly improve the appearance, and further maintains, on an excellent level, the electric properties of the resin blended therewith as a flame-retarding agent or smoke-suppressing agent. In particular, the zinc borate of the present invention improves the flame-retarding property of the chlorine-contained resins, nylons and epoxy resins.

EXAMPLES

In the following Examples, measurements were taken in accordance with the methods described below.
(1) Average particle diameter and particle sizes.

Average particle diameters and average particle sizes were measured by using a particle size analyzer, Model LS230, manufactured by Coulter Co.

(2) X-Ray diffraction.

Measured with Cu-Kα by using a Geigerflex RAD-B system manufactured by Rigaku Denki Co.

Target: Cu

Filter: Curved crystalline graphite monochrometer

Detector: SC

Voltage: 40 KV

Current: 20 mA

Full-scale count: 700 c/s

Smoothing point: 25

Scanning speed: 2°/min

Step sampling: 0.02°

Slit: DS 1° RS 0.15 mm SS 1°

Irradiation angle: 6°

(3) X-Ray diffraction condition in measuring crystallite size.

Measured with Cu-Kα by using a Geigerflex RAD-B system manufactured by Rigaku Denki Co.

Target: Cu

Filter: Ni

Tube voltage: 40 KV

Tube current: 20 mA

Full-scale count: 4 kcps

Scanning speed: 0.25°/min

Time constant: 0.5 sec

Slit: DS(SS) 0.50° RS 0.15 mm

Irradiation angle: 6°

Figure 25:
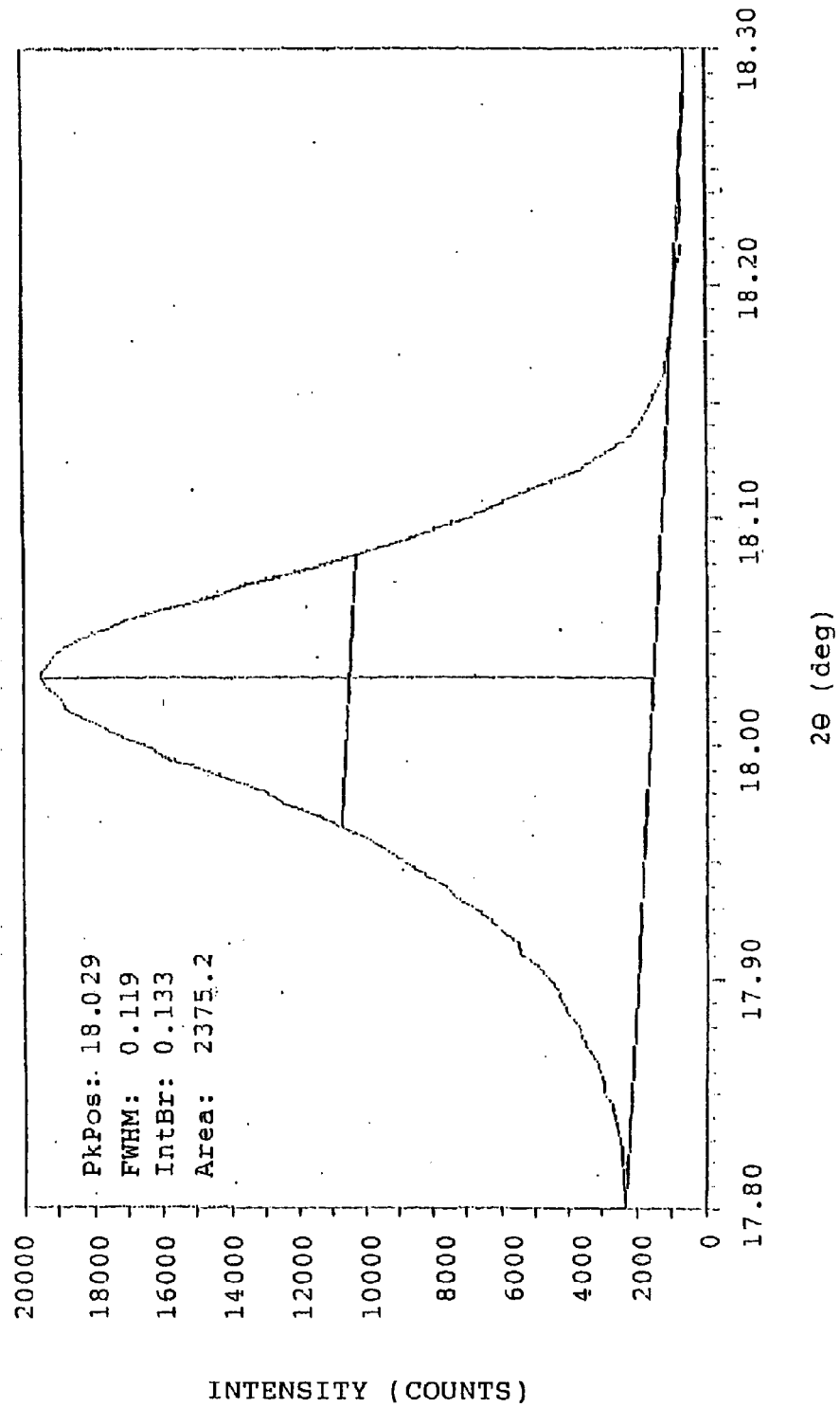
FIG. 25 shows a peak found by decreasing the scanning speed of an index of a plane (020) of FIG. 1, as a representative example for finding a half-value width of a diffraction peak.

FIG. 25 shows a peak from which an index of a plane (020) of FIG. 1 is found, as a representative example for finding a hald-value width of a diffraction peak.

(4) SEM measurement.

Measured by using a scanning electron microscope, S-570, manufactured by Hitachi, Ltd.

(5) Measurement of atomic absorbency.

Measured by using Z-8200 manufactured by Hitachi, Ltd.

(6) Chemical analysis

Conducted in compliance with the chemical analysis of lime stipulated under JIS R9011

Example 1

An aqueous solution was prepared by dissolving 72.5 g of boric acid ($B_2O_3$ content of 56.3%) in 1000 ml of pure water. To the aqueous solution were added 96.0 g of a zinc flower (ZnO content of 99.4%) and 217.5 g of boric acid ($B_2O_3$ content of 56.3%), and were stirred and mixed together such that the molar ratio of $B_2O_3$/ZnO was 2.0. Next, the solution was stirred and reacted at 60° C. for 90 minutes. The solution was further stirred and reacted at 90° C. for 4 hours. The obtained product was filtered, washed with water and was, then, dried at 105° C. to obtain a zinc borate (sample A-1). Table 3 shows the chemical composition and properties of the thus obtained zinc borate (sample A-1), FIG. 1 shows an X-ray diffraction image thereof, and FIGS. 2 and 3 show electron microphotographs thereof.

Example 2

Figure 4:
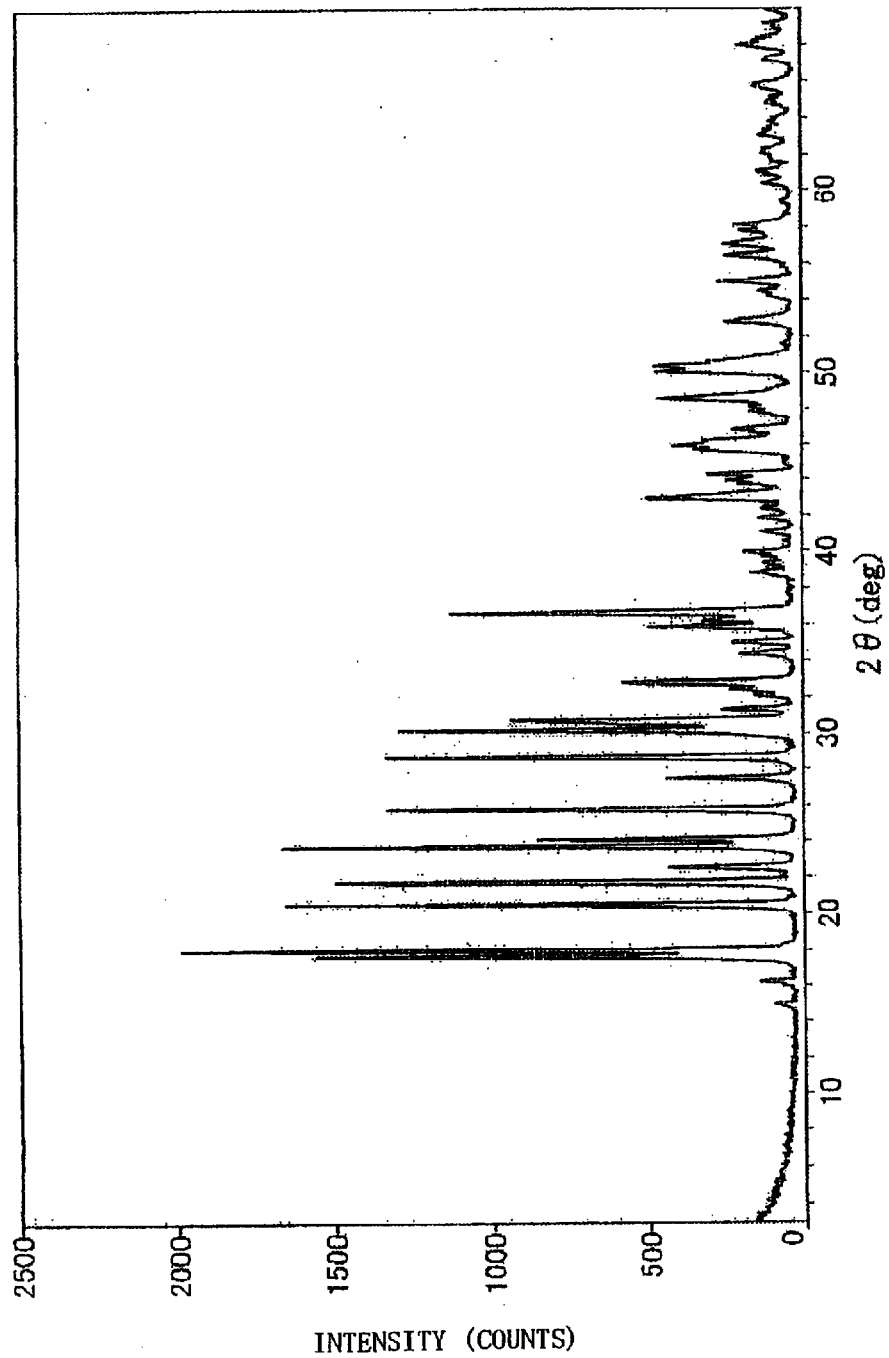
FIG. 4 is an X-ray diffraction image (Cu-kα) of a zinc borate according to an embodiment 2 of the present invention.

An aqueous solution was prepared by dissolving 72.5 g of boric acid ($B_2O_3$ content of 56.3%) in 1000 ml of pure water to which has been added 1.25 g of zinc borate ($2ZnO.3B_2O_3.3.5H_2O$) as a seed in advance. To the aqueous solution were added 95.7 g of a zinc flower (ZnO content of 99.4%) and 217.5 g of boric acid ($B_2O_3$ content of 56.3%), and were stirred and mixed together such that the molar ratio of $B_2O_3$/ZnO was 2.0. Next, the solution was stirred and reacted at 60° C. for 90 minutes. The solution was further stirred and reacted at 90° C. for 4 hours. The obtained product was filtered, washed with water and was, then, dried at 105° C. to obtain a zinc borate (sample A-2). Table 3 shows the chemical composition and properties of the thus obtained zinc borate (sample A-2), FIG. 4 shows an X-ray diffraction image thereof, and FIG. 5 shows an electron microphotograph thereof.

Example 3

Figure 7:
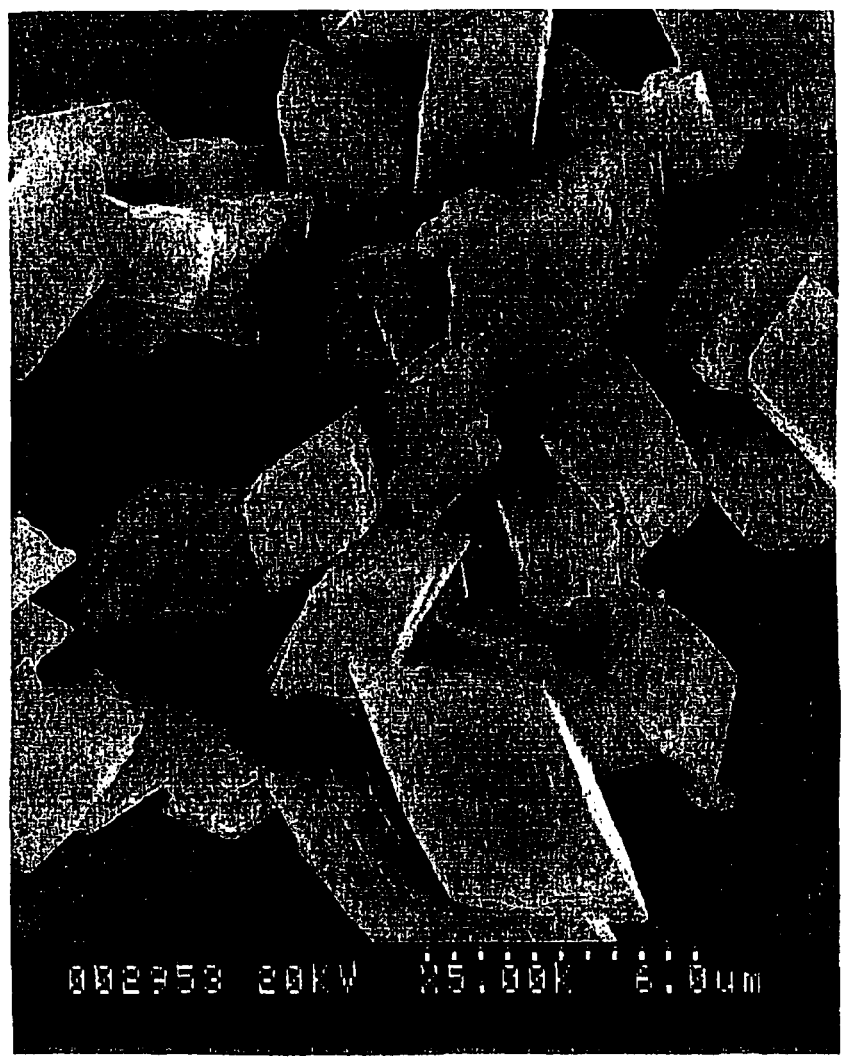
FIG. 7 is a scanning-type electron microphotograph (magnification: 5000 times) showing the particle structure of the zinc borate according to the embodiment 3 of the present invention.

An aqueous solution was prepared by dissolving 72.5 g of boric acid ($B_2O_3$ content of 56.3%) in 1000 ml of pure water. To the aqueous solution were added 95.7 g of a zinc flower (ZnO content of 99.4%) and 217.5 g of boric acid ($B_2O_3$ content of 56.3%), and were stirred and mixed together such that the molar ratio of $B_2O_3$/ZnO was 2.0. Next, the solution was stirred and reacted at 45° C. for 120 minutes. The solution was further stirred and reacted at 90° C. for 4 hours. The obtained product was filtered, washed with water and was, then, dried at 105° C. to obtain a zinc borate (sample A-3). Table 3 shows the chemical composition and properties of the thus obtained zinc borate (sample A-3), FIG. 6 shows an X-ray diffraction image thereof, and FIG. 7 shows an electron microphotograph thereof.

Example 4

Figure 8:
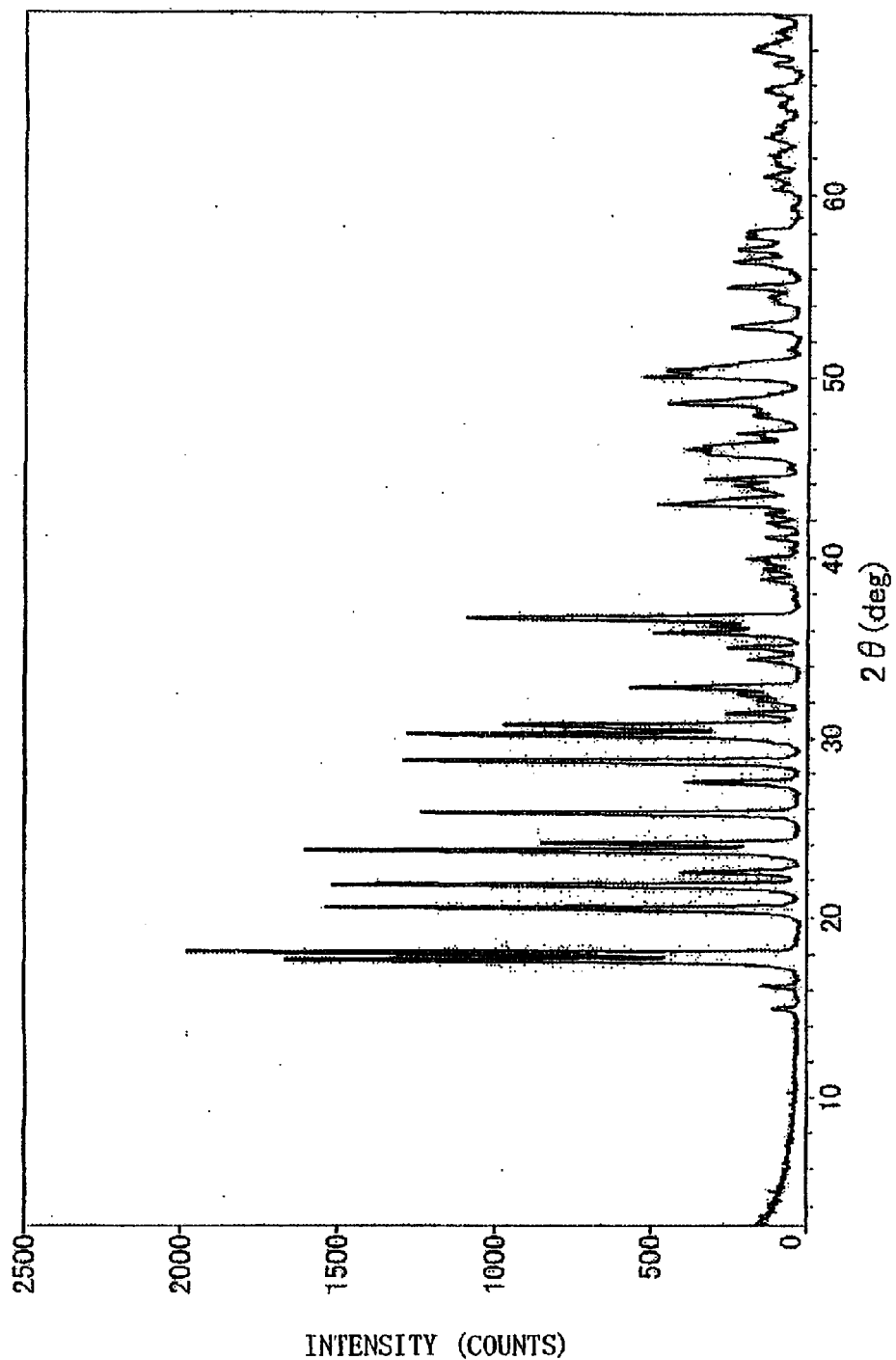
FIG. 8 shows an X-ray diffraction image (Cu-kα) of a zinc borate according to an embodiment 4 of the present invention.
Figure 9:
FIG. 9 is a scanning-type electron microphotograph (magnification: 5000 times) showing the particle structure of the zinc borate according to the embodiment 4 of the present invention.

An aqueous solution was prepared by dissolving 72.5 g of boric acid ($B_2O_3$ content of 56.3%) in 1000 ml of pure water. To the aqueous solution were added 95.7 g of a zinc flower (ZnO content of 99.4%) and 217.5 g of boric acid ($B_2O_3$ content of 56.3%), and were stirred and mixed together such that the molar ratio of $B_2O_3$/ZnO was 2.0. Next, the solution was stirred and reacted at 60° C. for 120 minutes. The solution was further stirred and reacted at 80° C. for 8 hours. The obtained product was filtered, washed with water and was, then, dried at 105° C. to obtain a zinc borate (sample A-4). Table 3 shows the chemical composition and properties of the thus obtained zinc borate (sample A-4), FIG. 8 shows an X-ray diffraction image thereof, and FIG. 9 shows an electron microphotograph thereof.

Example 5

Figure 10:
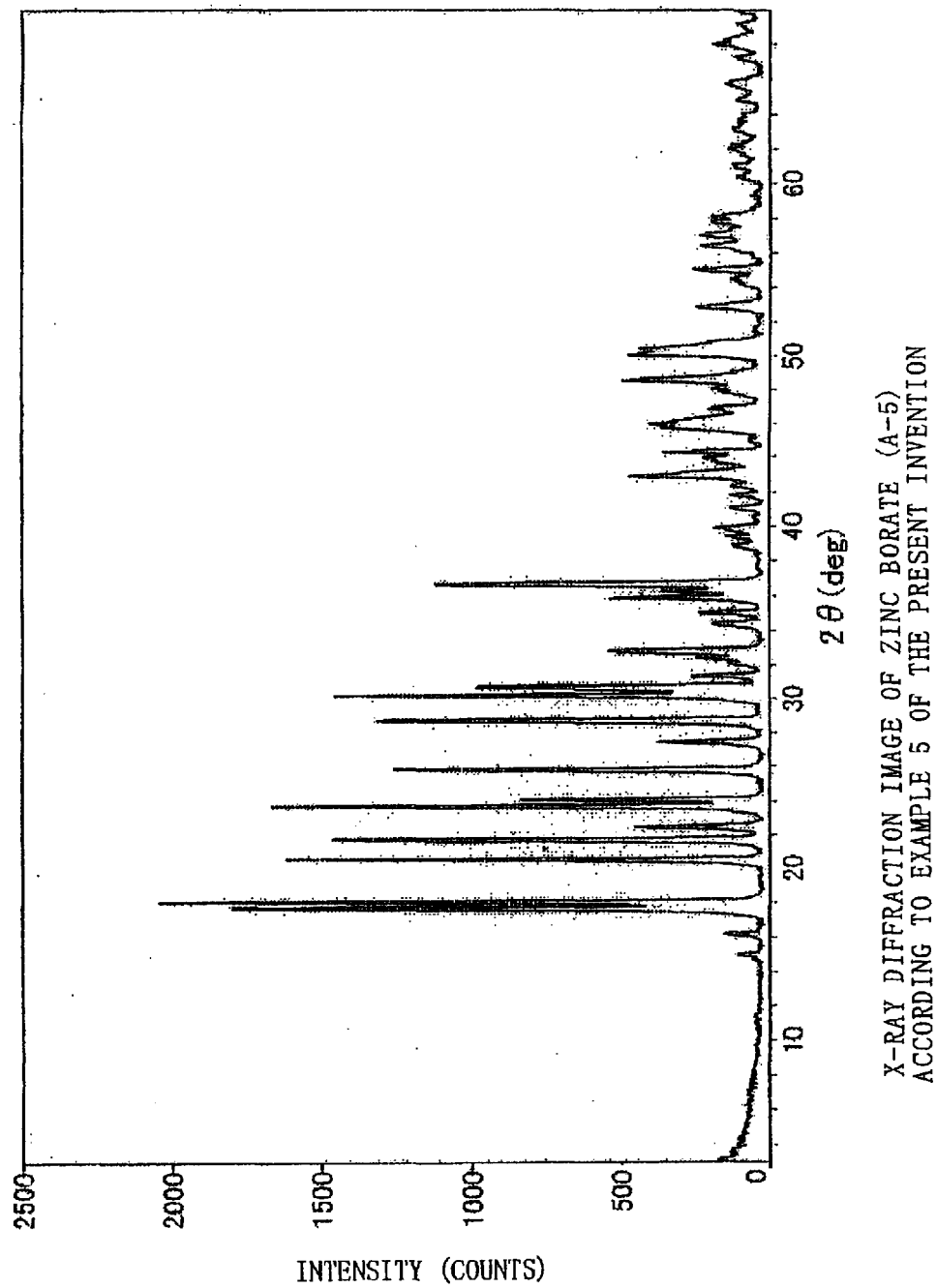
FIG. 10 shows an X-ray diffraction image (Cu-kα) of a zinc borate according to an embodiment 5 of the present invention.
Figure 11:
FIG. 11 is a scanning-type electron microphotograph (magnification: 5000 times) showing the particle structure of the zinc borate according to the embodiment 5 of the present invention.

An aqueous solution was prepared by dissolving 72.5 g of boric acid ($B_2O_3$ content of 56.3%) in 1000 ml of pure water. To the aqueous solution were added 95.7 g of a zinc flower (ZnO content of 99.4%) and 217.5 g of boric acid ($B_2O_3$ content of 56.3%), and were stirred and mixed together such that the molar ratio of $B_2O_3$/ZnO was 2.0. Next, the solution was stirred and reacted at 60° C. for 120 minutes. The solution was further stirred and reacted at 85° C. for 6 hours. The obtained product was filtered, washed with water and was, then, dried at 105° C. to obtain a zinc borate (sample A-5). Table 3 shows the chemical composition and properties of the thus obtained zinc borate (sample A-5), FIG. 10 shows an X-ray diffraction image thereof, and FIG. 11 shows an electron microphotograph thereof.

Example 6

Figure 12:
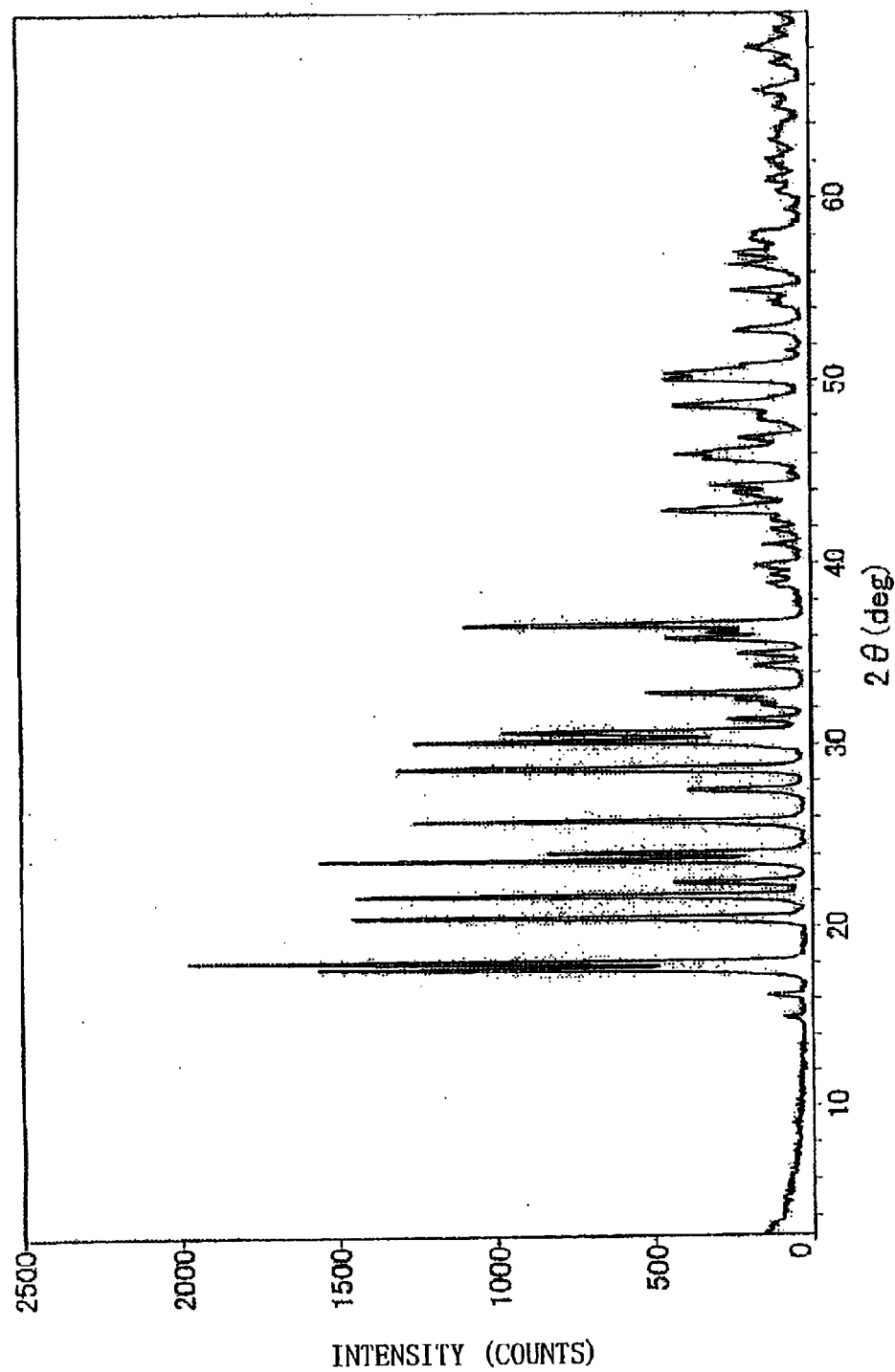
FIG. 12 shows an X-ray diffraction image (Cu-kα) of a zinc borate according to an embodiment 6 of the present invention.
Figure 13:
FIG. 13 is a scanning-type electron microphotograph (magnification: 5000 times) showing the particle structure of the zinc borate according to the embodiment 6 of the present invention.

An aqueous solution was prepared by dissolving 72.5 g of boric acid ($B_2O_3$ content of 56.3%) in 1000 ml of pure water to which has been added 1.25 g of zinc borate ($2ZnO.3B_2O_3.3.5H_2O$) as a seed in advance. To the aqueous solution were added 95.7 g of a zinc flower (ZnO content of 99.4%) and 217.5 g of boric acid ($B_2O_3$ content of 56.3%), and were stirred and mixed together such that the molar ratio of $B_2O_3$/ZnO was 2.0. Next, the solution was stirred and reacted at 65° C. for 80 minutes. The solution was further stirred and reacted at 90° C. for 4 hours. The obtained product was filtered, washed with water and was, then, dried at 105° C. to obtain a zinc borate (sample A-6). Table 3 shows the chemical composition and properties of the thus obtained zinc borate (sample A-6), FIG. 12 shows an X-ray diffraction image thereof, and FIG. 13 shows an electron microphotograph thereof.

Example 7

Figure 14:
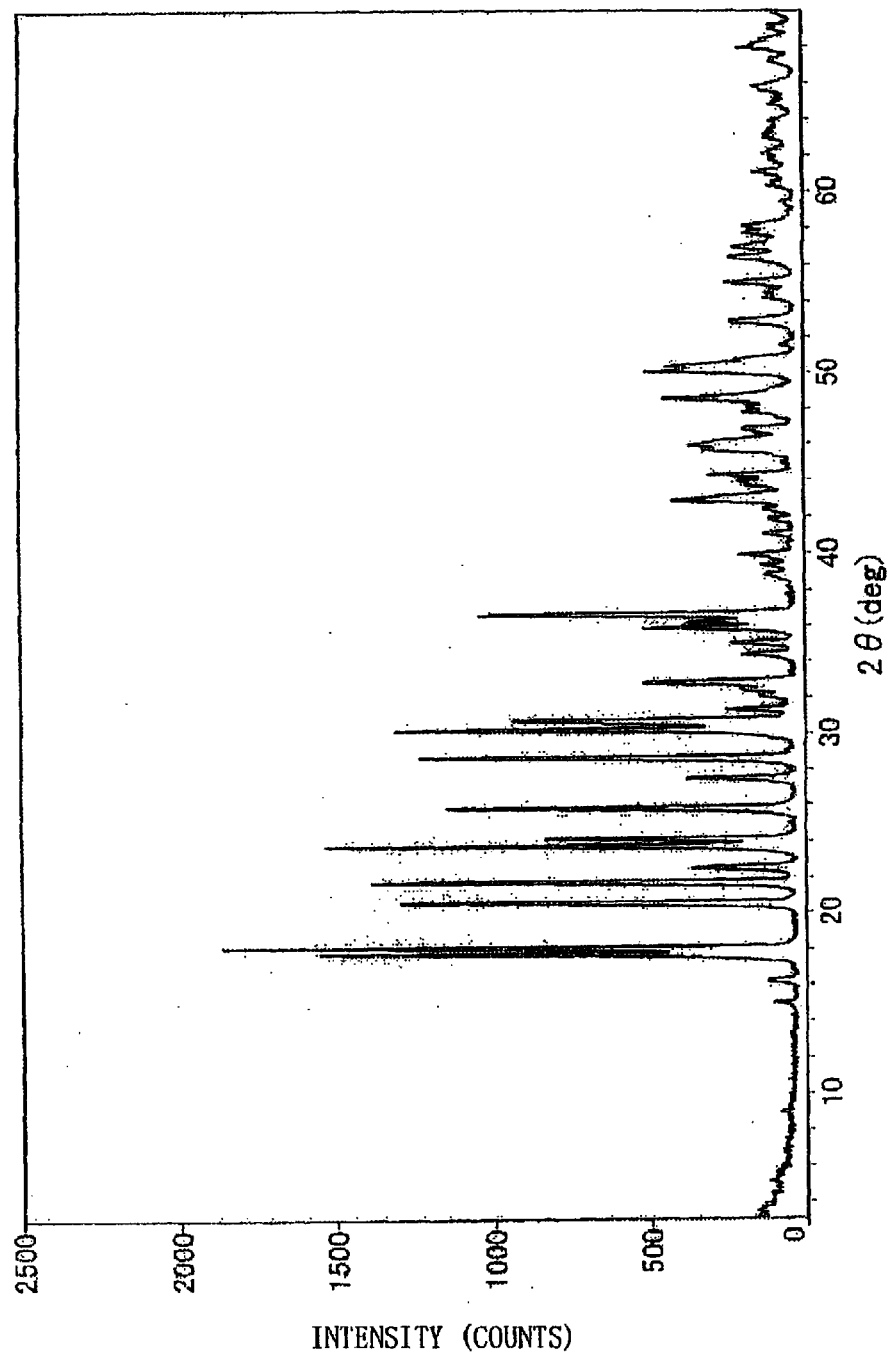
FIG. 14 shows an X-ray diffraction image (Cu-kα) of a zinc borate according to an embodiment 7 of the present invention.
Figure 15:
FIG. 15 is a scanning-type electron microphotograph (magnification: 5000 times) showing the particle structure of the zinc borate according to the embodiment 7 of the present invention.

An aqueous solution was prepared by dissolving 72.5 g of boric acid ($B_2O_3$ content of 56.3%) in 1000 ml of pure water. To the aqueous solution were added 95.7 g of a zinc flower (ZnO content of 99.4%) and 217.5 g of boric acid ($B_2O_3$ content of 56.3%), and were stirred and mixed together such that the molar ratio of $B_2O_3$/ZnO was 2.0. Next, the solution was stirred and reacted at 55° C. for 120 minutes. The solution was further stirred and reacted at 75° C. for 7 hours. The obtained product was filtered, washed with water and was, then, dried at 105° C. to obtain a zinc borate (sample A-7). Table 3 shows the chemical composition and properties of the thus obtained zinc borate (sample A-7), FIG. 14 shows an X-ray diffraction image thereof, and FIG. 15 shows an electron microphotograph thereof.

Example 8

Figure 16:
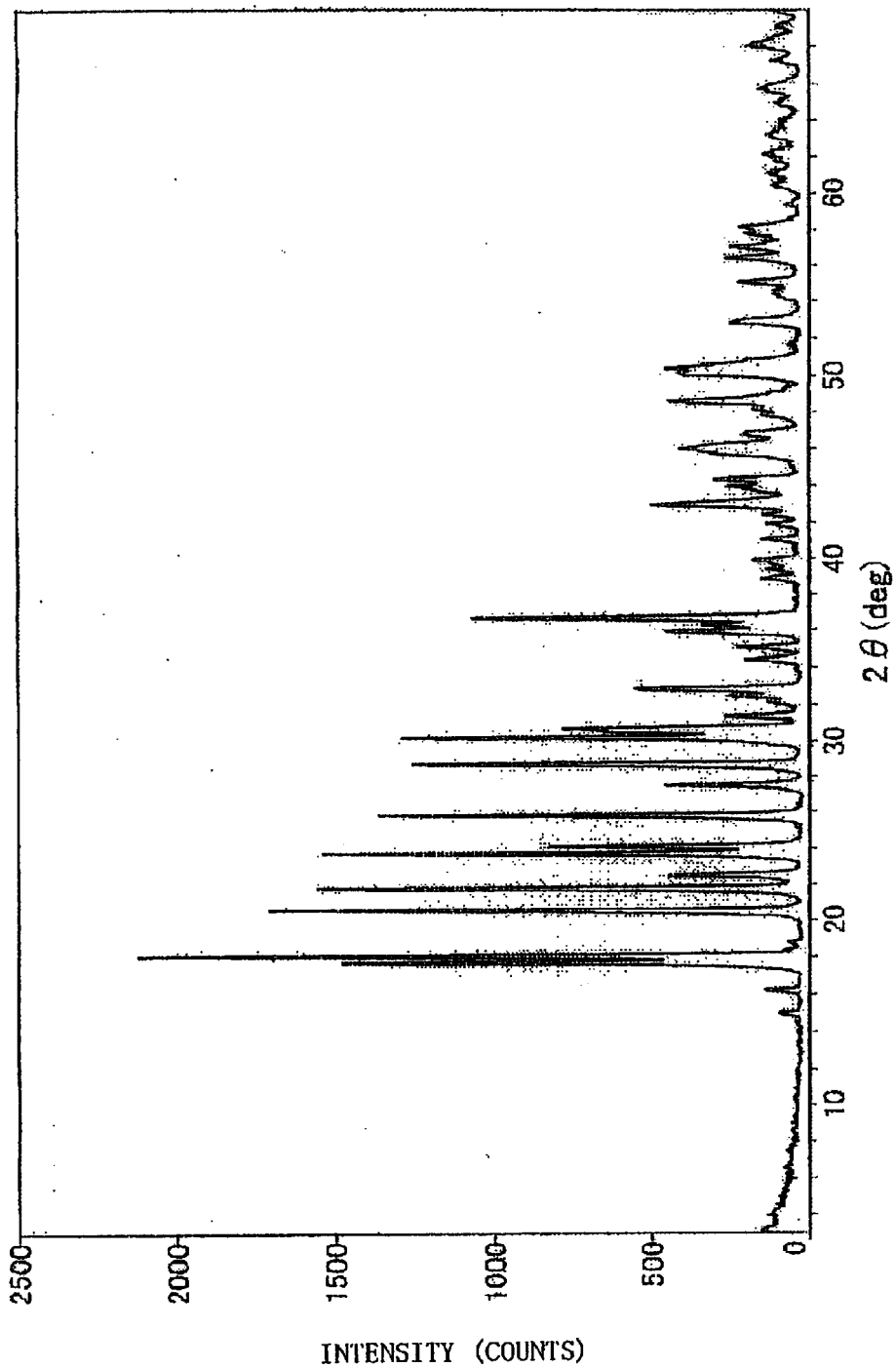
FIG. 16 shows an X-ray diffraction image (Cu-kα) of a zinc borate according to an embodiment 8 of the present invention.
Figure 17:
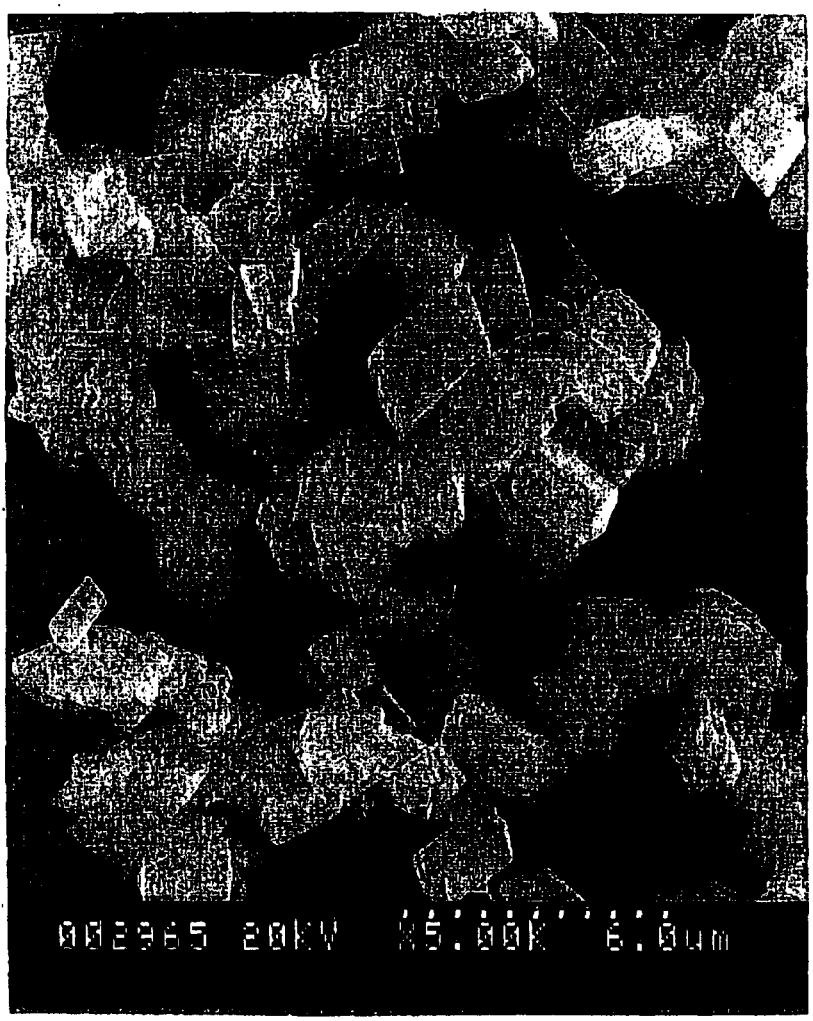
FIG. 17 is a scanning-type electron microphotograph (magnification: 5000 times) showing the particle structure of the zinc borate according to the embodiment 8 of the present invention.

An aqueous solution was prepared by dissolving 72.5 g of boric acid ($B_2O_3$ content of 56.3%) in 1000 ml of pure water. To the aqueous solution were added 95.7 g of a zinc flower (ZnO content of 99.4%) and 217.5 g of boric acid ($B_2O_3$ content of 56.3%), and were stirred and mixed together such that the molar ratio of $B_2O_3$/ZnO was 2.0. Next, the solution was stirred and reacted at 60° C. for 90 minutes. The solution was further stirred and reacted at 110° C. for 4 hours. The obtained product was filtered, washed with water and was, then, dried at 105° C. to obtain a zinc borate (sample A-8). Table 3 shows the chemical composition and properties of the thus obtained zinc borate (sample A-8), FIG. 16 shows an X-ray diffraction image thereof, and FIG. 17 shows an electron microphotograph thereof.

Comparative Example 1

Figure 18:
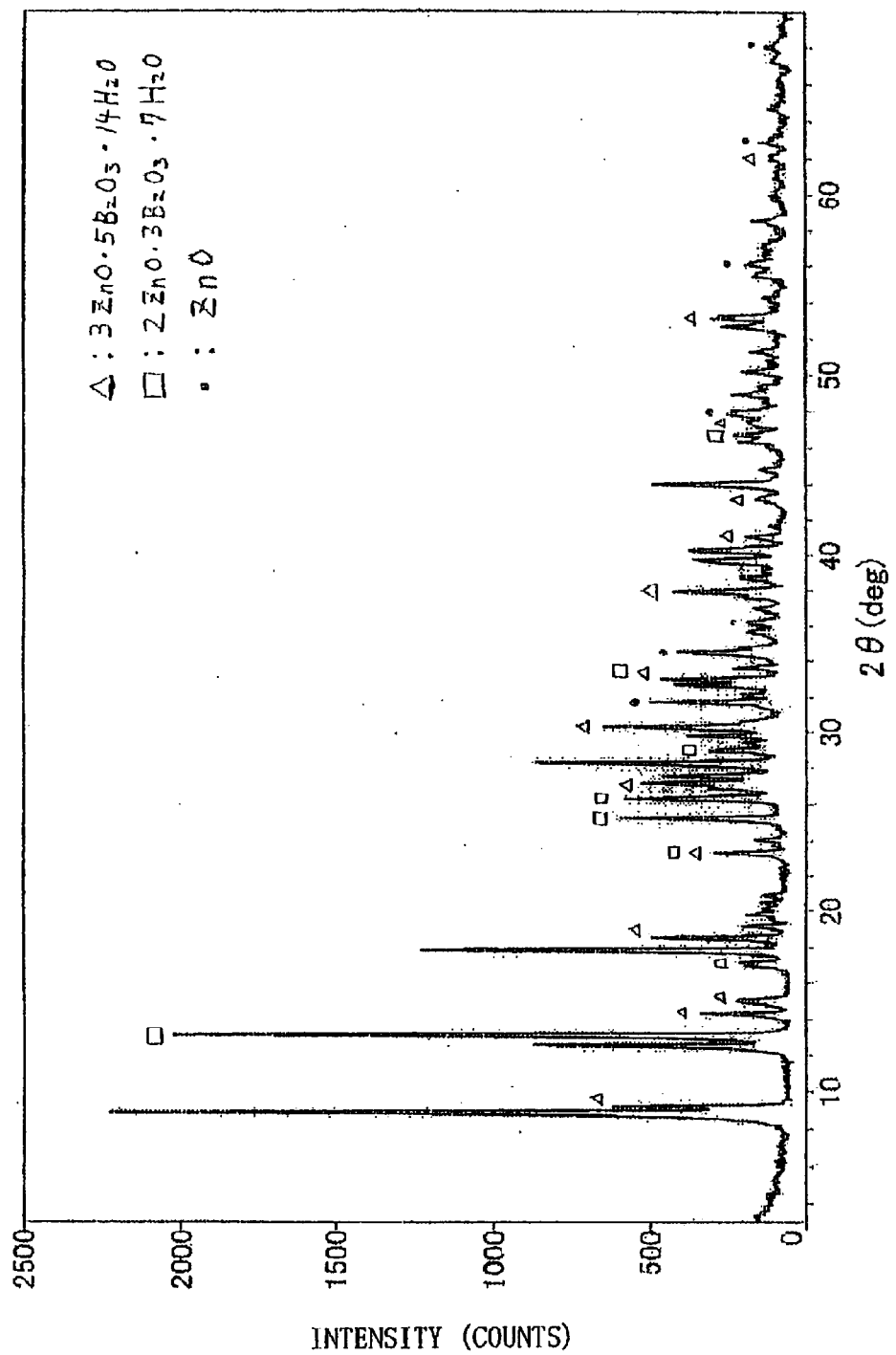
FIG. 18 shows an X-ray diffraction image (Cu-kα) of a zinc borate which is a comparative sample H-1.
Figure 19:
FIG. 19 is a scanning-type electron microphotograph (magnification: 5000 times) showing the particle structure of the zinc borate which is the comparative sample H-1.

An aqueous solution was prepared by dissolving 72.5 g of boric acid ($B_2O_3$ content of 56.3%) in 1000 ml of pure water. To the aqueous solution were added 95.7 g of a zinc flower (ZnO content of 99.4%) and 217.5 g of boric acid ($B_2O_3$ content of 56.3%), and were stirred and mixed together such that the molar ratio of $B_2O_3$/ZnO was 2.0. Next, the solution was stirred and reacted at 35° C. for 120 minutes. The solution was further stirred and reacted at 90° C. for 4 hours. The obtained product was filtered, washed with water and was, then, dried at 105° C. to obtain a zinc borate (sample H-1). Table 3 shows the chemical composition and properties of the thus obtained zinc borate (sample H-1), FIG. 18 shows an X-ray diffraction image thereof, and FIG. 19 shows an electron microphotograph thereof. From FIG. 18, the obtained zinc borate (sample H-1) was the one of the 2.3 type, but was in the form of mixed crystals of a heptahydrate ($2ZnO.3B_2O_3.7H_2O$) and a 3.5 type zinc borate ($3ZnO.5B_2O_3.14H_2O$), exhibiting a peak due to unreacted zinc oxide. The 2.3 type zinc borate was not obtained in a pure form.

Comparative Example 2

Figure 20:
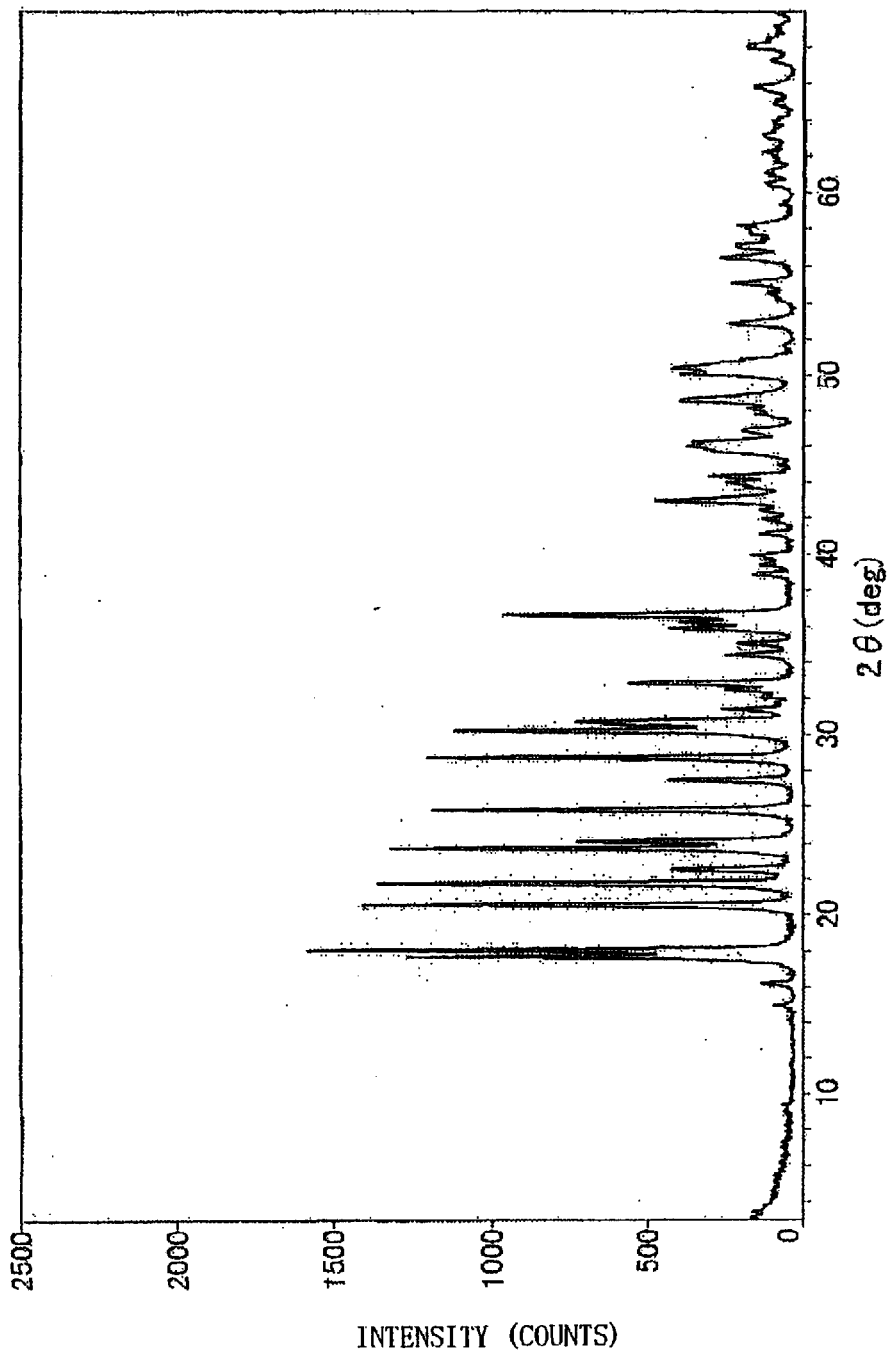
FIG. 20 shows an X-ray diffraction image (Cu-kα) of a zinc borate which is a comparative sample H-2.
Figure 21:
FIG. 21 is a scanning-type electron microphotograph (magnification: 5000 times) showing the particle structure of the zinc borate which is the comparative sample H-2.

An aqueous solution was prepared by dissolving 72.5 g of boric acid ($B_2O_3$ content of 56.3%) in 1000 ml of pure water. To the aqueous solution were added 95.7 g of a zinc flower (ZnO content of 99.4%) and 217.5 g of boric acid ($B_2O_3$ content of 56.3%), and were stirred and mixed together such that the molar ratio of $B_2O_3$/ZnO was 2.0. Next, the solution was stirred and reacted at 60° C. for 90 minutes. The solution was further stirred and reacted at 150° C. for 4 hours. The obtained product was filtered, washed with water and was, then, dried at 105° C. to obtain a zinc borate (sample H-2). Table 3 shows the chemical composition and properties of the thus obtained zinc borate (sample H-2), FIG. 20 shows an X-ray diffraction image thereof, and FIG. 21 shows an electron microphotograph thereof.

Comparative Examples 3 and 4

Figure 22:
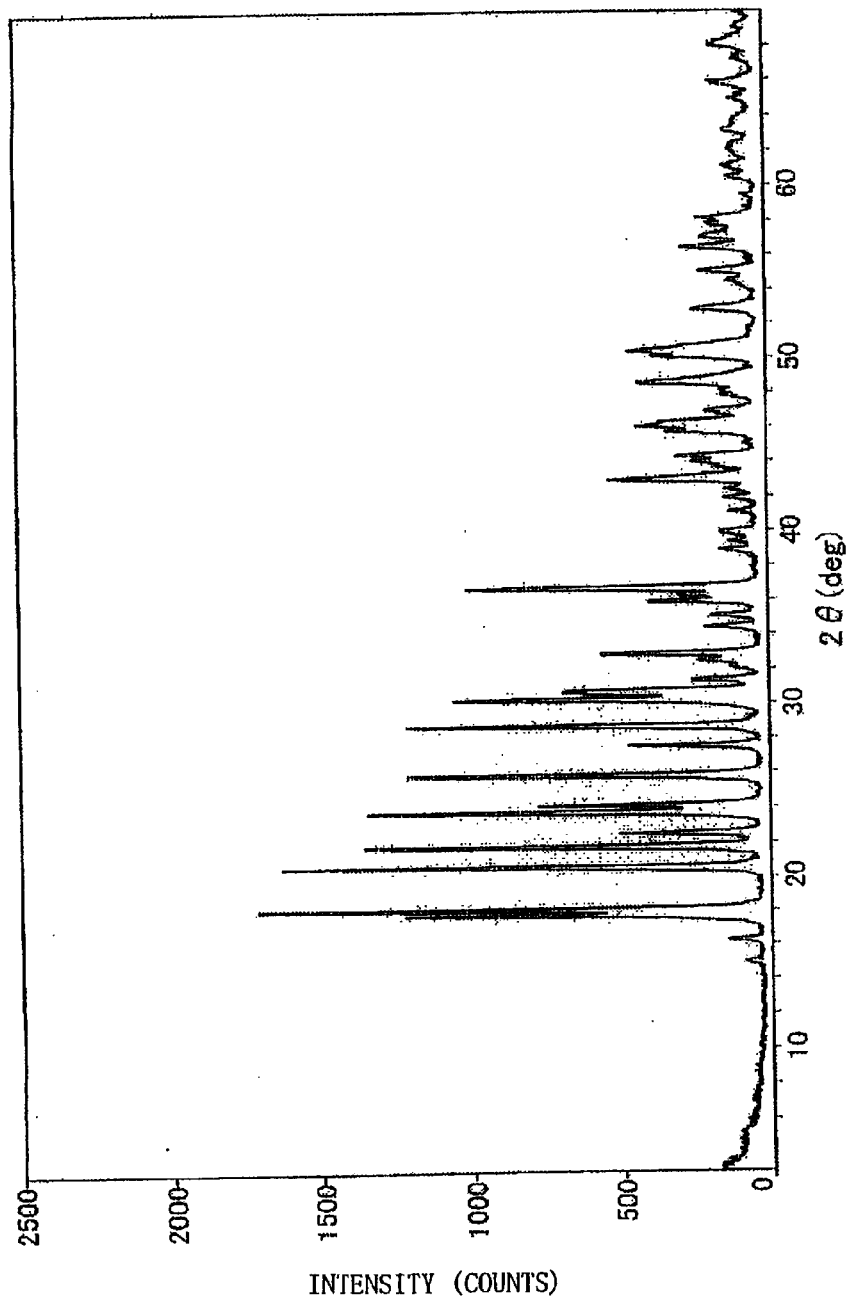
FIG. 22 shows an X-ray diffraction image (Cu-kα) of a commercially available zinc borate (comparative sample H-3) manufactured by company A.
Figure 23:
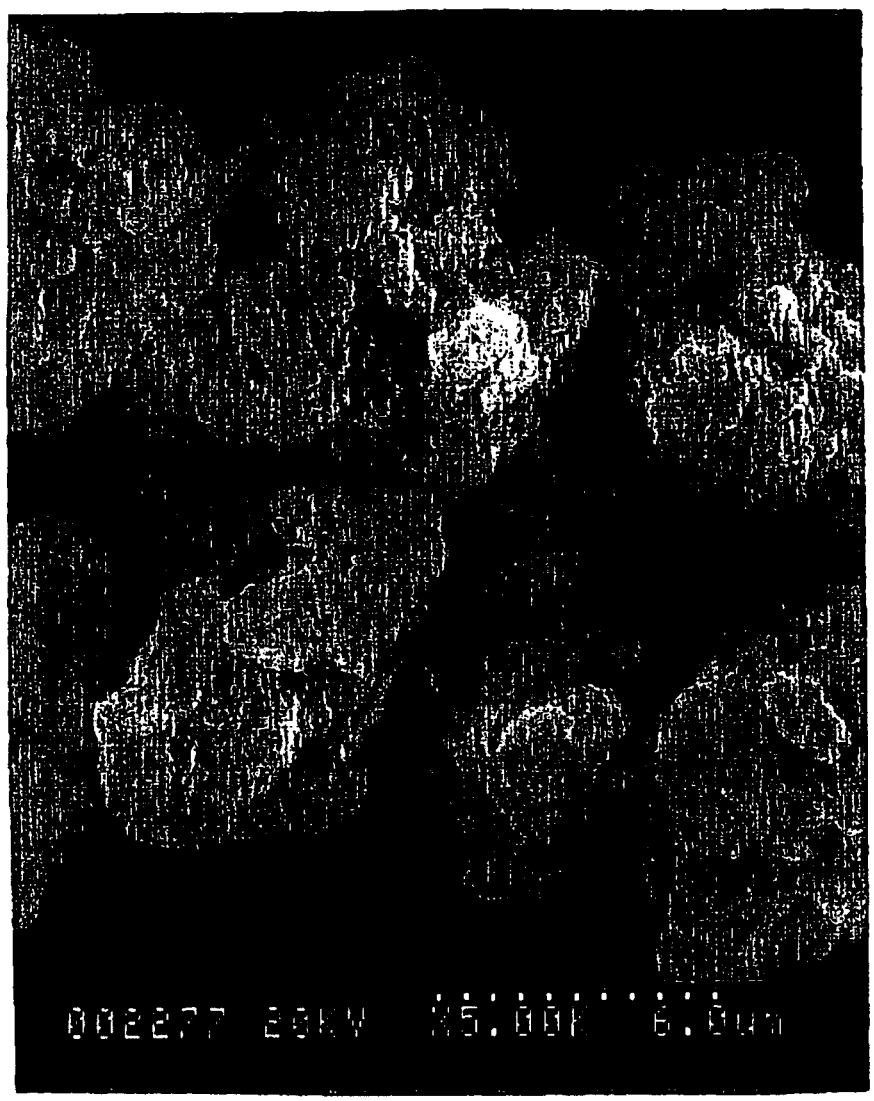
FIG. 23 is a scanning-type electron microphotograph (magnification: 5000 times) showing the particle structure of the commercially available zinc borate (comparative example H-3) manufactured by company A.
Figure 24:
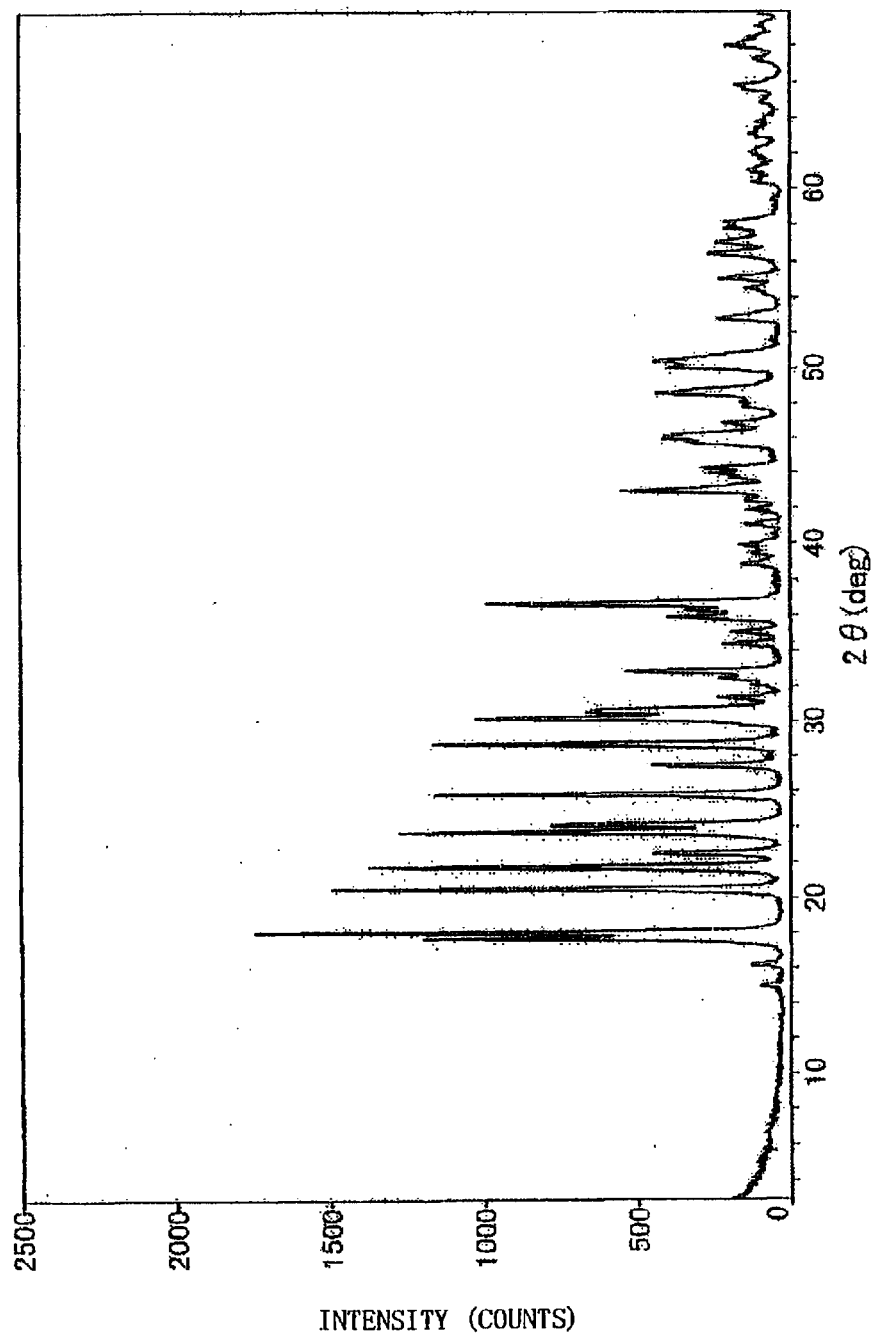
FIG. 24 shows an X-ray diffraction image (Cu-kα) of a commercially available zinc borate (comparative sample H-4) manufactured by company B.

Like in Example 1, Table 3 shows chemical compositions and physical properties of two kinds of zinc borates, i.e., a commercially available zinc borate (sample H-3) manufactured by company A and a commercially available zinc borate (sample H-4) manufactured by company B, FIG. 22 (H-3) and FIG. 24 (H-4) show X-ray diffraction images thereof, and FIG. 23 (H-3) shows an electron microphotograph thereof.

The evaluated results of the products of the invention will now be described in detail. The testing methods were as described below.

(1) Volume resistivity testing (V.R).

The following blend 1 was kneaded in a 3.5-inch roll mill at 160° C. for 7 minutes, and was pressed at 170° C. under 150 kg/cm² to prepare a sheet having a thickness of 1 mm.

The sheet was measured for its volume resistivity (ohms-cm) in compliance with the method stipulated under JIS K6723-6.8.

Blend 1:

| | |
|---|---|
| Vinyl chloride resin (P = 1300) | 100 parts |
| DINP (diisononyl phthalate) | 50 parts |
| Tribasic lead sulfate | 3.0 parts |
| Lead stearate | 0.5 parts |
| Sample | 5 to 15 parts |

(2) Limiting oxygen index (LOI).

The following blend 2 was kneaded in a 3.5-inch roll mill at 160° C. for 7 minutes, and was pressed at 170° C. under 150 kg/cm² to prepare a sheet having a thickness of 1 mm.

The sheet was measured for its limiting oxygen index (LOI value %) in compliance with the method stipulated under JIS K7201B by using a candle combustion tester manufactured by Toyo Seiki Mfg. Co. to evaluate the flame-retarding property.

Blend 2:

| | |
|---|---|
| Vinyl chloride resin (P = 1300) | 100 parts |
| DINP (diisononyl phthalate) | 50 parts |
| Tribasic lead sulfate | 3.0 parts |
| Lead stearate | 0.5 parts |
| Antimony trioxide | 0 to 10 parts |
| Zinc stannate | 0 to 10 parts |
| Sample | 1 to 15 parts |

Applied examples of the invention will now be described.

Examples 9 to 17

Table 4 below shows the results of the volume resistivity testing of the sample A-1 alone, and of the limiting oxygen index testing of when the sample A-1 and the antimony trioxide or the zinc stannate are used in combination.

Examples 18 to 32

In the blends 3 and 4 described below, the sample A-1, commercially available magnesium hydroxide, hydrotalcite, polyhydric alcohol, calcium hydroxide, calcium silicate, epoxy compound and fatty acid salt were introduced into a 7-liter magnetic pot mill at ratios shown in Table 5 together with 2.5 liters of magnetic balls of diameters of from 10 to 20 mm, and were ground and mixed for 5 hours, and were then pulverized by an atomizer to obtain about 300 g of a sample. Table 5 shows the results of the limiting oxygen index testing.

Comparative Examples 33 to 43

Test pieces were prepared at blending ratios shown in Table 6 under the conditions described above. The results are those of the limiting oxygen index testing of when antimony trioxide and zinc stannate are used in combination.

Comparative Examples 5 to 14

Table 7 below shows the results of the volume resistivity testing of the comparative sample H-3, and of the limiting oxygen index testing of when the comparative samples H-1, H-3, H-4 and the antimony trioxide or the zinc stannate are used in combination.

Examples 44 to 50 and Comparative Example 15

100 Parts by weight of a crosslinked polyethylene (NUC-9025) was blended with samples shown in Table 8, and the blends were kneaded at 105° C. for 5 minutes to prepare sheets. The obtained sheets were tested for their volume resistivities and limiting oxygen indexes. The results were as shown in Table 9. For comparison, there are also shown the results of a blank blended with none of them.

Examples 51 and 52 and Comparative Examples 16 to 18

100 Grams of a sodium silicate No. 3 was weighed into a polyethylene container, and into which were introduced 30 g of the sample A-1 or A-4 and, as Comparative Examples, boric acid, zinc flower and zinc phosphate each in 30 g. The mixture was lightly stirred, and the times were measured until the mixture was dispersed in the sodium silicate and the mixture was cured. The results were as shown in Table 8.

The dispersion property was observed by eyes until the mixture was cured, and was evaluated to be as follows:

⊚: Dispersed very well.

○: Dispersed well.

χ: Poorly dispersed causing the mixture to be separated or coagulated.

TABLE 3

| | Ex. 1 | Ex. 2 | Ex. 3 | Ex. 4 | Ex. 5 | Ex. 6 | Ex. 7 | Ex. 8 | Comp. Ex. 1 | Comp. Ex. 2 | Comp. Ex. 3 | Comp. Ex. 4 |
|---|---|---|---|---|---|---|---|---|---|---|---|---|
| Sample name | A-1 | A-2 | A-3 | A-4 | A-5 | A-6 | A-7 | A-8 | H-1 | H-2 | H-3 | H-4 |
| Seed | no | yes | no | no | no | no | yes | no | no | no | — | — |
| Synthesizing temp. (1St step) (° C.) | 60 | 60 | 45 | 60 | 60 | 65 | 55 | 60 | 35 | 60 | — | — |
| Synthesizing temp. (2Nd step) (° C.) | 90 | 90 | 90 | 80 | 85 | 90 | 75 | 110 | 90 | 150 | — | — |
| Crystallite size (020) (nm) | 67.6 | 90.0 | 78.9 | 89.2 | 92.6 | 73.5 | 63.3 | 82 | | 55.3 | 55.1 | 58.2 |
| Crystallite size (101) (nm) | 64.1 | 59.1 | 60.0 | 42.0 | 71.0 | 40.3 | 46.1 | 56.3 | | 51.1 | 50.1 | 52.5 |
| Crystallite size (200) (nm) | 64.5 | 73.5 | 70.7 | 78.3 | 82.2 | 86.1 | 88.0 | 76.1 | | 66.5 | 51.1 | 55.4 |
| Product of crystallite sizes ($nm^3$) | 279489 | 390947 | 334694 | 293343 | 540432 | 255033 | 256795 | 351323 | | 187918 | 141062 | 169274 |
| Median diameter ($\mu$m) | 2.8 | 2.7 | 2.9 | 3.4 | 3.2 | 3 | 2.5 | 3.1 | 4.3 | 3.2 | 8.6 | 3 |
| Na (ppm) | 15 | 20 | 18 | 16 | 16 | 15 | 19 | 16 | 25 | 17 | 348 | 230 |
| Mole ratio ($B_2O_3$/ZnO) | 1.49 | 1.50 | 1.47 | 1.49 | 1.48 | 1.49 | 1.46 | 1.51 | 1.40 | 1.50 | 1.51 | 1.49 |
| mole ratio ($H_2O$/ZnO) | 1.60 | 1.61 | 1.63 | 1.62 | 1.63 | 1.61 | 1.65 | 1.61 | 2.35 | 1.72 | 1.71 | 1.67 |

TABLE 4

(Examples using antimony trioxide and zinc stannate in combination)

| | Ex. 9 | Ex. 10 | Ex. 11 | Ex. 12 | Ex. 13 | Ex. 14 | Ex. 15 | Ex. 16 | Ex. 17 | Unit |
|---|---|---|---|---|---|---|---|---|---|---|
| PVC (P = 1300) | 100 | 100 | 100 | 100 | 100 | 100 | 100 | 100 | 100 | phr |
| DINP | 50 | 50 | 50 | 50 | 50 | 50 | 50 | 50 | 50 | phr |
| Tribasic lead sulfate | 3 | 3 | 3 | 3 | 3 | 3 | 3 | 3 | 3 | phr |
| Lead stearate | 0.5 | 0.5 | 0.5 | 0.5 | 0.5 | 0.5 | 0.5 | 0.5 | 0.5 | phr |
| Sample (A-1) | 10 | 5 | 5 | 3 | 10 | 5 | 5 | 3 | 2 | phr |
| $Sb_2O_3$ | | 10 | 5 | 7 | | | | | | phr |
| Zinc hydroxystannate (ZHS) | | | | | 3 | 10 | 5 | 7 | 8 | phr |
| O.I value | 25.7 | 33.0 | 30.0 | 30.5 | 28.2 | 32.5 | 28.0 | 29.2 | 30.0 | |
| V.R 30° C. ($\times 10^{13}$ $\Omega$cm) | 8.02 | | | | | | | | | |

TABLE 5

(Examples of coated products and of changing the amounts)

Test blend

| | |
|---|---|
| PVC (P = 1300) | 100 phr |
| DINP | 50 phr |
| Tribasic lead sulfate | 3.0 phr |
| Lead stearate | 0.5 phr |
| Sample | 10 phr |

| | Ex. 18 | Ex. 19 | Ex. 20 | Ex. 21 | Ex. 22 | Ex. 23 | Ex. 24 | Ex. 25 | Ex. 26 | Ex. 27 | Ex. 28 | Ex. 29 | Ex. 30 | Ex. 31 | Ex. 32 |
|---|---|---|---|---|---|---|---|---|---|---|---|---|---|---|---|
| Sample name | A-9 | A-10 | A-11 | A-12 | A-13 | A-14 | A-15 | A-16 | A-17 | A-18 | A-19 | A-20 | A-21 | A-22 | A-23 |
| Sample (A-1) | 10.0 | 9.70 | 9.70 | 9.70 | 9.70 | 9.70 | 9.70 | 9.70 | 9.50 | 9.50 | 9.50 | 9.50 | 9.50 | 9.50 | 9.50 |
| $Mg(OH)_2$ | | 0.30 | | | | | | | 0.5 | | | | | | |
| Polyhydric alcohol (dipentaerythritol) | | | 0.30 | | | | | | | 0.5 | | | | | |
| Hydrotalcite (Alkamizer 1) | | | | 0.3 | | | | | | | 0.5 | | | | |
| ESBO (epoxylated soy bean oil) | | | | | 0.3 | | | | | | | 0.5 | | | |
| $Ca(OH)_2$ | | | | | | 0.3 | | | | | | | 0.5 | | |
| Magnesium stearate | | | | | | | 0.3 | | | | | | | 0.5 | |
| Calcium silicate | | | | | | | | 0.3 | | | | | | | 0.5 |
| O.I value | 26.3 | 26.2 | 26.2 | 26.2 | 26.2 | 26.2 | 26.2 | 26.2 | 26.2 | 26.1 | 26.2 | 26.1 | 26.2 | 26.1 | 26.2 |

TABLE 6

(Examples of using coated products, amount-changed products, antimony trioxide and zinc stannate in combination)

(Test blend)

| | |
|---|---|
| PVC (P = 1300) | 100 phr |
| DINP | 50 phr |
| Tribasic lead sulfate | 3.0 phr |
| Lead stearate | 0.5 phr |
| Flame-retarding agent | 10–13 phr |

| | Ex. 33 | Ex. 34 | Ex. 35 | Ex. 36 | Ex. 37 | Ex. 38 | Ex. 39 | Ex. 40 | Ex. 41 | Ex. 42 | Ex. 43 |
|---|---|---|---|---|---|---|---|---|---|---|---|
| Sample (A-10) | 5 | 10 | | | | | | | | | |
| Sample (A-11) | | | 5 | | | | | | | | |
| Sample (A-12) | | | | 5 | 10 | | | | | | |
| Sample (A-16) | | | | | | 3 | | | | | |
| Sample (A-17) | | | | | | | 5 | 3 | | | |
| Sample (A-18) | | | | | | | | | 5 | | |
| Sample (A-19) | | | | | | | | | | 3 | |
| Sample (A-23) | | | | | | | | | | | 5 |
| Sb2O3 | 5 | | | 5 | | | 5 | | | 7 | |
| Zinc hydroxy stannate | | 3 | 5 | | 3 | 7 | | 7 | 5 | | 5 |
| O.I value | 30.0 | 28.2 | 28.0 | 30.0 | 28.1 | 29.8 | 30.0 | 29.8 | 28.0 | 30.4 | 28.0 |

TABLE 7

(Examples using antimony trioxide and zinc stannate in combination)

| | Comp. Ex. 5 | Comp. Ex. 6 | Comp. Ex. 7 | Comp. Ex. 8 | Comp. Ex. 9 | Comp. Ex. 10 | Comp. Ex. 11 | Comp. Ex. 12 | Comp. Ex. 13 | Comp. Ex. 14 | Unit |
|---|---|---|---|---|---|---|---|---|---|---|---|
| PVC (P = 1300) | 100 | 100 | 100 | 100 | 100 | 100 | 100 | 100 | 100 | 100 | phr |
| DINP | 50 | 50 | 50 | 50 | 50 | 50 | 50 | 50 | 50 | 50 | phr |
| Tribasic lead sulfate | 3 | 3 | 3 | 3 | 3 | 3 | 3 | 3 | 3 | 3 | phr |
| Lead stearate | 0.5 | 0.5 | 0.5 | 0.5 | 0.5 | 0.5 | 0.5 | 0.5 | 0.5 | 0.5 | phr |
| Sample (H-1) | | 5 | 5 | | | | | | | | phr |
| Sample (H-3) | 10 | | | 3 | 5 | | | 5 | 10 | | phr |
| Sample (H-4) | | | | | | 3 | 5 | | | 3 | phr |
| $Sb_2O_3$ | | 5 | | 7 | 5 | | | | | | phr |
| Zinc Hydroxystannate (ZHS) | | 5 | | | 7 | 5 | 5 | 5 | | 7 | phr |
| O.I value | 25.4 | 27.8 | 27.0 | 30.0 | 29.6 | 29.0 | 27.3 | 27.5 | 27.8 | 28.6 | |
| V.R 30° C. (× $10^{13}$ Ωcm) | | 4.06 | | | | | | | | | |

TABLE 8

| | Comp. Ex. 15 | Ex. 45 | Ex. 46 | Ex. 47 | Ex. 48 | Ex. 49 | Ex. 50 | Unit |
|---|---|---|---|---|---|---|---|---|
| Sample (A-1) | — | 10 | 20 | 40 | | | | phr |
| Sample (A-3) | — | | | | 10 | 20 | 40 | phr |
| O.I value | 18 | 19.5 | 20.8 | 23.8 | 19.3 | 20.5 | 23.2 | |
| V.R 30° C. (× $10^{17}$ Ωcm) | 2.6 | 1.5 | 1.3 | 1.0 | 1.1 | 1.0 | 0.5 | |

TABLE 9

(Curing property (at room temperature) of sodium silicate No. 3)

| | Example 51 | Example 52 | Comparative Example 16 | Comparative Example 17 | Comparative Example 18 |
|---|---|---|---|---|---|
| Sample name | A-1 | A-4 | boric acid | ZnO | zinc phosphate |
| Sodium silicate No. 3 | 100 | 100 | 100 | 100 | 100 |
| Sample (g) | 30 | 30 | 30 | 30 | 30 |
| Curing time | 13 min. | 18 min. | Readily cured | not cured | 35 hr |
| Dispersing property | ◉ | ◉ | X | ○ | X |

What is claimed is:

1. A zinc borate having a chemical composition represented by the following formula (1), $$2ZnO \cdot mB_2O_3 \cdot XH_2O \quad (1)$$

wherein m is a number of from 2.8 to 3.2, and x is a number of not larger than 4, and having a crystallite size of not smaller than 40 nm as found from diffraction peaks of indexes of planes of (020), (101) and (200) in the X-ray diffraction (Cu-kα) and containing sodium components in amounts of not larger than 100 ppm as measured by the atomic absorptiometric method.

2. A zinc borate according to claim 1, wherein the individual particles are independent rhombic hexahedrons, the length of a side of each particle lying in a range of from 0.3 to 7.0 μm as measured by a scanning-type electron microphotograph.

3. A method of preparing a zinc borate by forming fine crystals of a zinc borate by reacting a zinc flower and a boric acid at a substantially stoichiometric ratio at a relatively low temperature, effecting the aging as required and, then, maintaining the reaction system at a relatively high temperature to grow the crystals.

4. A resin composition containing a thermoplastic resin and/or a thermosetting resin as well as a zinc borate having a chemical composition represented by the following formula (1), $$2ZnO \cdot mB_2O_3 \cdot XH_2O \quad (1)$$

wherein m is a number of from 2.8 to 3.2, and x is a number of not larger than 4, and having a crystallite size of not smaller than 40 nm as found from diffraction peaks of indexes of planes of (020), (101) and (200) in the x-ray diffraction (Cu-kα) and containing sodium components in amounts of not larger than 100 ppm as measured by the atomic absorptiometric method.

5. A resin composition according to claim 4, wherein the zinc borate is contained in an amount of from 1 to 150 parts by weight per 100 parts by weight of the resin.

6. A zinc borate according to claim 1 wherein a product crystallite sizes as found from the diffraction peaks of indexes of planes (020), (101) and (200) is not smaller than 200,000 $nm^3$.

7. A zinc borate according to claim 2 wherein a product of crystallite sizes as found from the diffraction peaks of indexes of planes (020), (101) and (200) is not smaller than 200,000 $nm^3$.

8. A zinc borate according to claim 1 wherein a volume-based median diameter as found by a laser diffraction method is in a range of from 1.0 to 6.0 μm.

9. A zinc borate according to claim 7 wherein a volume-based median diameter as found by a laser diffraction method is in a range of from 1.0 to 6.0 μm.

10. A flame-retarding agent or a flame-retarding assistant comprising the zinc borate of claim 1.

11. A flame-retarding agent or a flame-retarding assistant comprising the zinc borate of claim 8.

12. A flame-retarding agent or a flame-retarding assistant comprising the zinc borate of claim 9.

13. A smoke-suppressing agent comprising the zinc borate of claim 1.

14. A smoke-supressing agent comprising the zinc borate of claim 8.

15. A smoke-suppressing agent comprising the zinc borate of claim 9.

16. An antibacterial agent comprising the zinc borate of claim 1.

17. An antibacterial agent comprising the zinc borate of claim 8.

18. An antibacterial agent comprising the zinc borate of claim 9.

19. A water glass-curing agent comprising the zinc borate of claim 1.

20. A water glass-curing agent comprising the zinc borate of claim 8.

21. A water glass-curing agent comprising the zinc borate of claim 9.

* * * * *